(12) United States Patent
Amanullah

(10) Patent No.: US 10,504,761 B2
(45) Date of Patent: Dec. 10, 2019

(54) METHOD SYSTEM FOR GENERATING 3D COMPOSITE IMAGES OF OBJECTS AND DETERMINING OBJECT PROPERTIES BASED THEREON

(71) Applicant: Semiconductor Technologies and Instruments Pte. Ltd., Singapore (SG)

(72) Inventor: Ajharali Amanullah, Singapore (SG)

(73) Assignee: SEMICONDUCTOR TECHNOLOGIES & INSTRUMENTS PTE. LTD., Singapore (SG)

( * ) Notice: Subject to any disclaimer, the term of this patent is extended or adjusted under 35 U.S.C. 154(b) by 47 days.

(21) Appl. No.: 15/890,338

(22) Filed: Feb. 6, 2018

(65) Prior Publication Data

US 2018/0226283 A1 Aug. 9, 2018

Related U.S. Application Data

(60) Provisional application No. 62/610,236, filed on Dec. 25, 2017, provisional application No. 62/456,258, filed on Feb. 8, 2017.

(51) Int. Cl.
*H01L 21/67* (2006.01)
*G06T 7/00* (2017.01)
(Continued)

(52) U.S. Cl.
CPC . *H01L 21/67288* (2013.01); *G01N 21/95684* (2013.01); *G06T 7/0004* (2013.01);
(Continued)

(58) Field of Classification Search
CPC .............. H01L 21/67288; H01L 22/12; G01N 21/95684; G06T 7/0004; G06T 2207/30148; G06T 2200/04
See application file for complete search history.

(56) References Cited

U.S. PATENT DOCUMENTS 8,224,062 B2 * 7/2012 Ohkura .............. G01N 21/9505
382/149
9,324,178 B2 * 4/2016 Cheng .................. G01N 23/203
(Continued)

OTHER PUBLICATIONS

Yano, Yuji, et al. "Three-dimensional very thin stacked packaging technology for SiP." 52nd Electronic Components and Technology Conference 2002.(Cat. No. 02CH37345). IEEE, 2002. (Year: 2002).*

*Primary Examiner* — Bobbak Safaipour
(74) *Attorney, Agent, or Firm* — Horizon IP Pte Ltd.

(57) ABSTRACT

A 3D object inspection process includes: capturing an object bottom surface 3D profile (a) while an object top surface freely rests on an object seating surface, or (b) without forcibly compressing the top surface of the object against a reference structure distinct from a suction tip; capturing an object top surface 3D profile while (c) the object bottom surface freely rests on the object seating surface, or (d) without forcibly compressing the bottom surface of the object against the reference structure; capturing a plurality of object sidewall images; generating a 3D composite image comprising a 3D digital reconstruction or estimation of the object based upon or using a bottom surface 3D profile image dataset, a top surface 3D profile image dataset, and the sidewall image dataset; and determining a set or array of total object and/or object main body contour values and/or thickness values from the 3D composite image.

18 Claims, 14 Drawing Sheets

(51) Int. Cl.
*G01N 21/956* (2006.01)
*H01L 21/66* (2006.01)

(52) U.S. Cl.
CPC .......... *H01L 22/12* (2013.01); *G06T 2200/04* (2013.01); *G06T 2207/30148* (2013.01)

(56) References Cited

U.S. PATENT DOCUMENTS

| | | | | |
|---|---|---|---|---|
| 2005/0255610 | A1* | 11/2005 | Sato | G01B 7/08 |
| | | | | 438/14 |
| 2010/0188486 | A1* | 7/2010 | Amanullah | G01N 21/8806 |
| | | | | 348/48 |
| 2015/0060669 | A1* | 3/2015 | Cheng | G01N 23/203 |
| | | | | 250/310 |
| 2019/0033233 | A1* | 1/2019 | Amanullah | G01N 21/8806 |

* cited by examiner

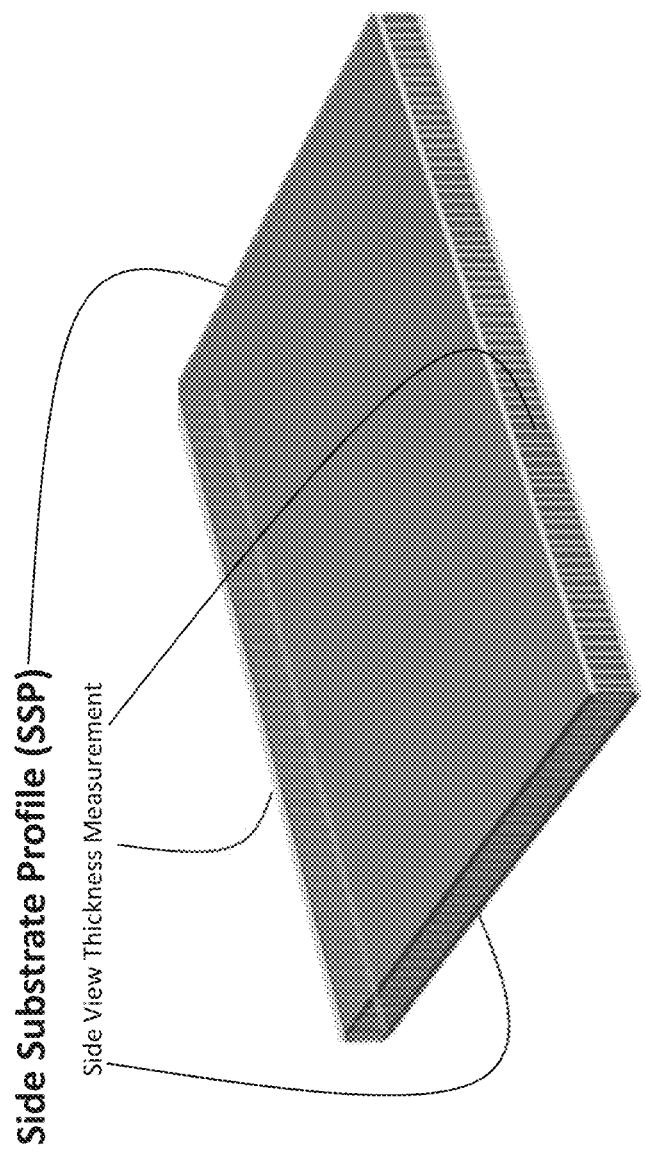

Evaluation Results (14x18mm)

| Device No | Top Warpage (TWP) | Bottom Warpage (BWP) | Total Pkg Thickness (TPT) | Side Substrate Profile (SSP) | | True Mold Thickness (TMT) | |
|---|---|---|---|---|---|---|---|
| | | | | Max | Min | Max | Min |
| 1 | 25.8 | 19.3 | 1108.4 | 758.48 | 747.02 | 786 | 732 |
| 2 | 20.7 | 18.4 | 1113.6 | 759.09 | 749.87 | 772 | 740 |
| 3 | 27.2 | 16.3 | 1119.3 | 759.36 | 749.12 | 787 | 713 |
| 4 | 24.5 | 18.9 | 1123.8 | 758.68 | 750.89 | 792 | 694 |
| 5 | 20.6 | 11.5 | 1102.3 | 760.99 | 742.07 | 781 | 741 |
| 6 | 22.4 | 15.1 | 1089.3 | 756.04 | 747.70 | 771 | 730 |
| 7 | 18.2 | 16.3 | 1087.4 | 764.45 | 742.55 | 779 | 747 |

1. Achieve 3Sigma Repeatability of 5um for individual Measurements such as TPT, TWP, BWP and SSP
2. Achieve 3Sigma Repeatability of 10um for combined measurements such as TMT

FIG. 9B

Accuracy Correlation With Golden Units

1. Use 4 GUs with Different Surface Topology for Accuracy Verification
2. Measure TPT using Top3D Camera
3. Measure TMT using Bottom3D, Top3D and 4-Side Cameras
4. Achieve Accuracy of <5um for Total Package Thickness Measurement
5. Achieve Accuracy of <10um for True Mold Thickness Measurement Total Package Thickness (TPT)

| GU | Scope (um) | Hexa 3D (um) | Deviation (um) |
|---|---|---|---|
| 1 | 1149 | 1150.6 | 2.6 |
| 2 | 1182 | 1183.8 | 1.8 |
| 3 | 1016 | 1018.7 | 2.7 |
| 4 | 1050 | 1054.4 | 4.4 |
| | | Average Deviation | 2.9 |

True Mold Thickness (TMT)

| GU | Scope (um) | | Hexa 3D (um) | | Deviation (um) | |
|---|---|---|---|---|---|---|
| | Max | Min | Max | Min | Max | Min |
| 1 | 1148 | 1004 | 1152 | 1010 | 4 | 6 |
| 2 | 1182 | 1020 | 1185 | 1025 | 3 | 5 |
| 3 | 1016 | 846 | 1013 | 853 | 3 | 7 |
| 4 | 1050 | 889 | 1056 | 897 | 6 | 8 |
| | | | | Average Deviation | 4 | 6.5 |

FIG. 10

METHOD SYSTEM FOR GENERATING 3D COMPOSITE IMAGES OF OBJECTS AND DETERMINING OBJECT PROPERTIES BASED THEREON

TECHNICAL FIELD

Aspects of the present disclosure relate to automated or computerized three dimensional (3D) optical inspection of objects. More particularly, aspects of the present disclosure are directed to the automated, automatic, or computer-based optical inspection of objects involving the generation, derivation, or calculation and storage of a top surface of curvature image and a bottom surface of curvature image of an object; the capture and storage of a plurality of object sidewall images; the generation, synthesis or derivation and storage of a 3D composite image of the object by way of digitally registering or aligning and unifying, integrating, or joining/connecting the top surface curvature of surface image, the bottom surface of curvature image, and the sidewall images; and the subsequent performance of one or more object inspection, characterization, or evaluation processes using the generated 3D composite image.

BACKGROUND

Electronic device manufacturers attempt to fit or squeeze as many integrated circuit devices as possible into the limited real estate of larger devices manufactured therewith, for instance, mobile devices such as mobile phones, which themselves are getting progressively thinner and more compact over time due to market preferences and demands. Presently, mobile device manufacturers compete based on producing ever more powerful yet smaller, slimmer and more compact devices. Consequently, more often than not, multiple integrated circuit devices, chips, or die are embedded or stacked into a single semiconductor component package, thereby forming what can be defined as a packaged composite device. There is a greater likelihood that one or more portions of a packaged composite device can become warped, distorted, or too thick during the course of its manufacture. This affects the ability of the manufacturer to accurately ascertain whether the packaged composite device will meet dimensional and reliability requirements prior to mounting the packaged composite device into or onto portions of a slim mobile device. Furthermore, the extent of and profile of the warpage or distortion of the packaged composite devices inspected may indicate problems in the manufacturing process, such as errors in device embedding or stacking. If a package is exceedingly thick, it may indicate that the multiple devices stacked in the package may not have been correctly stacked, or may indicate poor adhesion or mounting during the manufacturing process.

In the past, in association with the optical inspection of packaged composite devices, manufacturers relied on Total Package Thickness (TPT) as a parameter or measure of the thickness or height of the packaged composite device, the measurement of which includes the height of the underlying ball grid array or pads for the package. This parameter alone has become insufficient to accurately determine if a package will fit and/or likely reliably operate in a mobile device, as the possible manners in which a packaged composite device can dimensionally vary as a result of manufacturing process inconsistencies and/or errors can result in the false rejection of acceptable or good devices, as well as the acceptance or passage of defective or likely unreliable devices when relying on TPT as the sole measure for characterizing packaged composite device height.

With respect to optical inspection, warpage of the package together with how the package is seated or held in position during an inspection process may result in a larger package height reading, which may cause the package to be rejected even though the package may actually be mountable in or on a mobile device, as the slightly elastic nature of the package mold compound allows for some compression and flattening of the package and the devices contained therein without affecting the electrical or structural integrity of the entire package.

Conventional optical inspection of packaged devices such as packaged composite devices requires the packaged device to be suction or vacuum-held by a nozzle against a planar reference surface during inspection. This results in compression of the package against the reference surface. The resultant distortion of the package as a result of compression against the plane of the reference surface can either increase the package warpage (thereby artificially increasing the actual TPT) or reduce the package warpage (thereby artificially reducing the actual TPT) during inspection, resulting in erroneous TPT measurements or readings. It must be noted that if a 3D scan is performed on the top and/or bottom surfaces of a package when held against a reference plane or held down at the inspection area by vacuum or suction force against a reference seating plane, the captured 3D profile of the top and/or bottom surfaces of the package will not provide the correct or required surface topology of the package.

It is necessary to find a way for manufacturers to determine if a packaged composite device meets the dimensional requirements for it to be mounted and reliably used in a slim mobile device without the problems, limitations, and inconsistencies mentioned above.

SUMMARY

In accordance with an aspect of the present disclosure, a 3D object inspection process includes: capturing an object bottom surface 3D profile (a) while an object top surface freely rests on an object seating surface, or (b) without forcibly compressing the top surface of the object against a reference structure distinct from a suction tip; capturing an object top surface 3D profile while (c) the object bottom surface freely rests on the object seating surface, or (d) without forcibly compressing the bottom surface of the object against the reference structure; capturing a plurality of object sidewall images; generating a 3D composite image comprising a 3D digital reconstruction or estimation of the object based upon or using a bottom surface 3D profile image dataset, a top surface 3D profile image dataset, and the sidewall image dataset; and determining a set or array of total object and/or object main body contour values and/or thickness values from the 3D composite image.

In accordance with particular aspects of the present disclosure, a process is directed to 3D inspection of objects, where each object includes a main body having a top surface, a bottom surface, and a plurality of sidewalls vertically extending between the top surface and the bottom surface of the object in a z-axis direction, and the process includes: capturing a 3D profile image of the object bottom surface and generating a corresponding bottom surface 3D profile image dataset while (a) the object top surface freely rests upon a first object seating surface and the object is not subjected to external compressive forces other than the force of gravity, or (b) the object top surface is held by a first suction tip by way of suction force and forcible compression of the top surface of the object against a first reference structure distinct from a first suction tip is avoided; capturing a 3D profile image of the object top surface and generating a corresponding top surface 3D profile image dataset while (c) the object bottom surface freely rests upon the first or a second object seating surface and the object is not subjected to external compressive forces other than the force of gravity, or (d) the object bottom surface is held by the first or a second suction tip by way of suction force and forcible compression of the bottom surface of the object against each of the first reference structure and a second reference structure distinct from the second suction tip is avoided; capturing a plurality of sidewall images of the object and generating a corresponding sidewall image dataset; and generating a 3D composite image dataset corresponding to a 3D digital reconstruction or estimation of the object based upon or using the bottom surface 3D profile image dataset, the top surface 3D profile image dataset, and the sidewall image dataset.

The bottom surface 3D profile image dataset is generated by way of a bottom surface 3D scan line imaging procedure performed across the area of the bottom surface of the object, and the top surface 3D profile image dataset is generated by way of a top surface 3D scan line imaging procedure performed across the area of the top surface of the object.

The first object seating surface can be planar with respect to the surface area of at least one of the top surface and the bottom surface of the object, and/or the second object seating surface can be planar with respect to the surface area of at least one of the top surface and the bottom surface of the object.

The object top surface can freely rest upon the first object seating surface and the object is not subjected to external compression forces other than the force of gravity during the capture of the 3D profile image of the object bottom surface, and (c) the object bottom surface can freely rest upon the first or a second object seating surface and the object is not subjected to external compressive forces other than the force of gravity during the capture of the 3D profile image of the object top surface.

Alternatively, while capturing the 3D bottom surface profile, (a) the object top surface can freely rest upon the first object seating surface and the object is not subjected to external compression forces other than the force of gravity during the capture of the 3D profile image of the object bottom surface, and while capturing the 3D top surface profile, and (d) the object bottom surface can be held by the first or the second suction tip by way of suction force and forcible compression of the bottom surface of the object against each of the first reference structure and a second reference structure is avoided; or while capturing the 3D bottom surface profile, (b) the object top surface can be held by the first suction tip by way of suction force and forcible compression of the top surface of the object against the first reference structure is avoided, and while capturing the 3D top surface profile(c) the object bottom surface can freely rest upon one of first seating structure and the second seating structure.

The object includes or can be a packaged semiconductor device, and one of the 3D profile images of the object top surface object bottom surface can be captured while the object sits in a carrier, platform, or medium having a standardized design with respect to the semiconductor industry and which is used for storing or transporting packaged semiconductor devices. The standard carrier, platform, or medium can include or be one of an industry standard tray, an industry standard boat, or an industry standard tape structure configured for carrying packaged semiconductor devices of predetermined sizes.

Generating the 3D composite image dataset can include generating each of a bottom surface of curvature image dataset and a top surface of curvature image dataset. Generating the bottom surface of curvature image dataset can include: numerically determining an array of (x, y) values that defines a reference bottom surface plane corresponding to the physical bottom surface of the object; and numerically determining z-axis deviations between the bottom surface 3D profile image dataset and the reference bottom surface plane for each (x, y) value within the array of (x, y) values within the reference bottom surface plane.

The process can further include storing the z-axis deviations between the bottom surface 3D profile image dataset and the bottom surface reference plane for each (x, y) value as a bottom surface profile (BSP) dataset comprising an (x, y) array of bottom surface profile values corresponding to physical object top surface non-uniformity relative to the z-axis.

Generating the top surface of curvature image dataset can include: numerically determining an array of (x, y) values that defines a reference top surface plane corresponding to the physical top surface of the object; and numerically determining z-axis deviations between the top surface 3D profile image dataset and the reference bottom surface plane for each (x, y) value within the array of (x, y) values within the reference bottom surface plane.

The process can further include storing the z-axis deviations between the top surface 3D profile image dataset and the top surface reference plane for each (x, y) value as a top surface profile (TSP) dataset comprising an (x, y) array of top surface profile values corresponding to physical object top surface non-uniformity relative to the z-axis.

Generating the 3D composite image dataset can further include digitally aligning or registering the BSP dataset, the TSP dataset, and the sidewall image dataset relative to each other, and stitching together the digitally aligned or registered BSP dataset, TSP dataset, and sidewall dataset.

The process can further include generating a True Object Main Body Thickness (TOMBT) dataset in which any given TOMBT(x, y) value represents a z-axis distance between the TSP and the BSP within the 3D composite image at a specific (x, y) point.

The process can further include determining a Total Object Thickness (TOT) value by way of analysing the 3D profile image of the object bottom surface and the 3D profile image of the object top surface; and determining a largest z-axis distance between a lowest physical object structure in the 3D profile image of the object bottom surface and a highest physical object structure in the 3D profile image of the object top surface.

In accordance with a particular aspect of the present disclosure, a system is directed to 3D inspection of objects, where each object includes a main body having a top surface, a bottom surface, and a plurality of sidewalls vertically extending between the top surface and the bottom surface of the object in a z-axis direction, where the apparatus includes: a set of 3D object imaging or scanning stations configured for imaging or scanning each of the object bottom surface and the object top surface and generating a 3D object bottom surface dataset and a 3D object top surface dataset, respectively, by way of: (i) capturing a 3D profile image of the object bottom surface and generating a corresponding bottom surface 3D profile image dataset while (a) the object top surface freely rests upon a first object seating surface and the object is not subjected to external compressive forces other than the force of gravity, or (b) the object top surface is held by a first suction tip by way of suction force and forcible compression of the top surface of the object against a first reference structure distinct from a first suction tip is avoided; and (ii) capturing a 3D profile image of the object top surface and generating a corresponding top surface 3D profile image dataset while (c) the object bottom surface freely rests upon the first or a second object seating surface and the object is not subjected to external compressive forces other than the force of gravity, or (d) the object bottom surface is held by the first or a second suction tip by way of suction force and forcible compression of the bottom surface of the object against each of the first reference structure and a second reference structure distinct from the second suction tip is avoided; an object sidewall scanning station configured for imaging or scanning a plurality of object sidewalls; at least one processing unit; and a memory storing program instructions configured for generating a 3D composite image dataset corresponding to a 3D digital reconstruction or estimation of the object based upon or using the bottom surface 3D profile image dataset, the top surface 3D profile image dataset, and the sidewall image dataset.

The set of 3D object imaging or scanning stations can include at least one 3D scan line profile imaging apparatus, and the object sidewall scanning station can include an apparatus configured for simultaneously imaging or scanning multiple object sidewalls.

BRIEF DESCRIPTION OF THE DRAWINGS

FIG. 6 indicates a representative plurality of 2D sidewall images captured in association with aspects of 3D optical inspection of a packaged semiconductor device in accordance with an embodiment of the present disclosure.

FIG. 8C shows particular evaluation or measurement results based on 3D composite images generated in accordance with an embodiment of the present disclosure for seven actual 11.5 mm×13 mm packages.

FIG. 9B shows particular evaluation or measurement results based on 3D composite images generated in accordance with an embodiment of the present disclosure for seven actual 14 mm×18 mmm packages.

FIG. 10 shows measurement comparisons between (a) 3D optical inspection measurements based on 3D composite images generated in accordance with an embodiment of the present disclosure, and (b) measurements made using an optical microscope for reference or "Golden Unit" packages.

DETAILED DESCRIPTION

Figure 1:
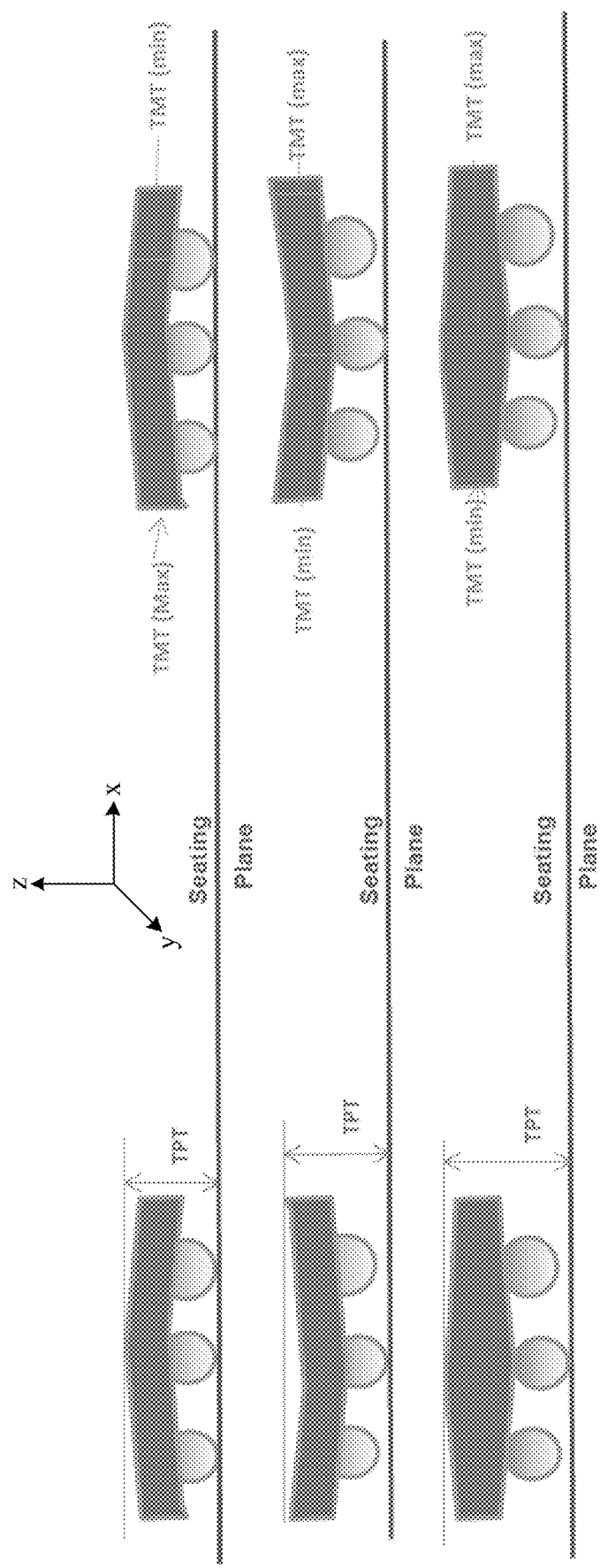
FIG. 1 illustrates particular representative types of packaged object parameters corresponding to semiconductor devices that reside in a molded package (e.g., packaged composite devices), including Total Package Thickness (TPT) and Total Mold Thickness (TMT) parameters, which can be estimated, determined, calculated, or measured in accordance with various embodiments of the present disclosure.

In the present disclosure, the depiction of a given element or consideration or use of a particular element number in a particular FIG. or a reference thereto in corresponding descriptive material can encompass the same, an equivalent, or an analogous element or element number identified in another FIG. or descriptive material associated therewith. The presence of "/" in a FIG. or text herein outside of its use in the phrase "and/or" is understood to mean "and/or" as conventionally defined (e.g., both or either of two stated selections, possibilities, or choices), unless otherwise indicated. The recitation of a particular numerical value or value range herein is understood to include or be a recitation of an approximate numerical value or value range, for instance, within +/−20%, +/−15%, +/−10%, +/−5%, +/−2%, or +/−0%. The term "essentially" or "essentially all" can indicate a percentage or level of equivalence greater than or equal to 90%, for instance, 95%, 98%, 99%, or 100%.

As used herein, the term "set" corresponds to or is defined as a non-empty finite organization of elements that mathematically exhibits a cardinality of at least 1 (i.e., a set as defined herein can correspond to a unit, singlet, or single element set, or a multiple element set), in accordance with known mathematical definitions (for instance, in a manner corresponding to that described in *An Introduction to Mathematical Reasoning: Numbers, Sets, and Functions*, "Chapter 11: Properties of Finite Sets" (e.g., as indicated on p. 140), by Peter J. Eccles, Cambridge University Press (1998)). In general, an element of a set can include or be a system, an apparatus, a device, a structure, an object, a process, a physical parameter, or a value depending upon the type of set under consideration.

Embodiments in accordance with the present disclosure relate or are directed to methods and systems for automated, automatic, computer-based, or computerized 3D optical inspection of objects such as semiconductor or other components. In at least some situations, objects that are undergoing, will undergo, or which require 3D optical inspection in accordance with an embodiment of the present disclosure include or have associated therewith a package or package structure (e.g., an external or outer package structure). For instance, semiconductor components can include or be molded packages containing one or more semiconductor die or integrated circuit chips or devices therein, e.g., packaged or packaged composite semiconductor devices (which may be referred to hereafter as packages or packaged devices).

In various embodiments, a given object under consideration has a first, upper, or top surface; a second, lower, or bottom surface; and a set of peripheral or side surfaces or sidewalls that separates the upper/top surface and the lower/bottom surface from each other. With respect to a representative set of orthogonal (x, y, z) axes and a selectable/selected, preferred, or predetermined reference spatial orientation of the object in relation thereto, the top surface and the bottom surface of the object can be defined to extend laterally or horizontally across portions of an (x, y) plane defined by the x-axis and the y-axis, and can exhibit positive and/or negative height variations across the (x, y) plane along portions of the z-axis (i.e., perpendicular to the (x, y) plane). The set of object sidewalls can be defined to project in a z-axis direction or extend along portions of the z-axis between the object's top and bottom surfaces, and any given sidewall can be defined to have a sidewall height profile with respect to an (x, z) or (y, z) plane. Moreover, any given sidewall can exhibit z-axis height variations along the sidewall's x-axis or y-axis extent (e.g., length).

In several (though not necessarily all) embodiments, objects to be inspected or undergoing inspection for purpose of determining Total Package Thickness (TPT) and/or True Mold Thickness (TMT) parameters or values in accordance with an embodiment of the present disclosure include or are molded semiconductor packages or packaged composite devices carrying structures such as solder bumps that extend beyond a main package body defined by the package top surface, bottom surface, and sidewalls. For instance, with respect to packages that include solder bumps, each package can be defined to have a top surface; a bottom surface from which the solder bumps project; and four sidewalls. As indicated in FIG. 1, in such a situation TPT indicates, establishes, or measures a maximum z-axis distance or height from a lowest or bottom-most solder ball point of a given packaged composite device to a highest or upper-most point on the top surface of the packaged composite device, in a manner readily understood by individuals having ordinary skill in the art. Objects to be inspected or undergoing inspection in accordance with an embodiment of the present disclosure can alternatively include or be molded semiconductor packages or packaged composite devices carrying peripheral lead wires or leads, in a manner readily understood by individuals having ordinary skill in the relevant art In accordance with embodiments of the present disclosure, in association with or during the optical inspection of a packaged device for purpose of determining TPT and/or TMT, one or more optical imaging procedures or operations can occur (a) in the absence of the application of any external or extrinsic mechanical, suction/vacuum, and non-gravitational forces to the packaged device, such that portions of the packed device are imaged while the packaged device retains its natural, intrinsic, as-manufactured, freely-resting, non-extrinsically distorted, or non-distorted shape or 3D profile; and/or (b) the absence of the application of external or extrinsic mechanical, suction/vacuum, and non-gravitational forces to the packaged device that could or would significantly distort the packaged device relative to its natural, intrinsic, as-manufactured, freely-resting, non-extrinsically distorted, or non-distorted shape or 3D profile, such that portions of the packaged device are imaged while the packaged device retains or essentially retains its natural, intrinsic, as-manufactured, freely-resting, non-extrinsically distorted, or non-distorted shape or 3D profile even while being retained or held in a predetermined position or orientation (e.g., by way of a pick-up tip or head that applies a suction/vacuum force across a limited or predetermined maximum portion of the package's surface area).

Thus, in accordance with various embodiments of the present disclosure, one or more optical imaging procedures or operations performed in association with determining TPT and/or TMT values (e.g., optical scan line or thin line illumination based 3D profile generation) can occur while the packaged device freely or naturally rests upon a support or seating surface or plane. Additionally or alternatively, particular optical imaging procedures or operations performed in association with determining TPT and/or TMT values (e.g., optical scan line or thin line illumination based 3D profile generation) can occur while the packaged device is carried or held in a manner that reduces or minimizes the likelihood of or which essentially or effectively avoids deformation of the packaged composite device relative to its natural, intrinsic, as-manufactured, freely-resting, non-extrinsically distorted, or non-distorted shape or 3D profile, such that enhanced accuracy determination of TPT and/or TMT values can occur.

Embodiments in accordance with the present disclosure entirely avoid the compression (e.g., mechanical or suction/vacuum force based compression) of entire or large portions of packaged device surface areas against a planar reference surface during optical imaging or inspection, such as during the optical imaging of top and bottom packaged device surfaces. Moreover, while imaging one or more surfaces of a packaged device, embodiments in accordance with the present disclosure can entirely avoid (a) the application of non-gravitational as well as external or extrinsic mechanical compressive forces to the packaged device, and/or the (b) application of external or extrinsic suction/vacuum forces across more than 5%-50% (e.g., more than 10%, 15% 20%, 25%, 30%, 35%, 40%, or 45%) of the area of a particular packaged device surface, such as the area of largest packaged device surface. Rather, in accordance with various embodiments of the present disclosure, one or more 3D profiles or images of a package or packaged device are captured or generated while the package is or remains in its natural, freely resting state, and/or one or more 3D profiles or images of the package are captured or generated while the package is carried or held in a manner that avoids the application of non-gravitational compressive forces to the package as well as the application of suction/vacuum forces to the package across more than 5%-50% (e.g., more than 10%, 15%, 20%, 25%, 30%, 35%, 40%, or 45%) of the surface area of the top surface or the bottom surface of the package.

As indicated in FIG. 1 and further detailed below, in various embodiments TMT parameters, values, or measurements include a set of values that indicates, establishes, or measures at least a maximum (TMT max), a minimum (TMT min) z-axis height or thickness of the mold compound(s) forming the main body of the package itself, between the 3D topographic profile or contour of the top surface of the package and the 3D topographic surface profile or contour of the bottom surface of the package, exclusive or net of the thicknesses of the solder balls or other structures that project away from the package mold compound(s) along a vertical direction such as lead wires. A TPT parameter or measurement includes or is a value that indicates, establishes, or measures a maximum z-axis height or thickness of the molded package plus the solder balls (or other types of structures that project away from the package mold compound(s) along a vertical direction) carried thereby.

The inventor named on the present application realized that instead of 3D surface profiles generated, captured, or obtained when an object such as a packaged semiconductor component or device (e.g., a packaged composite device) is intentionally compressed against a planar reference surface, what is actually needed in order to facilitate enhanced-accuracy or most-accurate determination of actual 3D package characteristics and corresponding package suitability for downstream use is the generation of 3D surface profiles obtained while compression of the package against a planar reference surface is entirely avoided, or compression of significant portions of the surface area of a package against a planar reference surface is avoided, such that during 3D imaging operations the package remains in its natural, intrinsic, as-manufactured, freely-resting, non-extrinsically distorted, or non-distorted shape or 3D profile, or the package remains in a state that is essentially, effectively, or very nearly identical to its natural, intrinsic, as-manufactured, freely-resting, non-extrinsically distorted, or non-distorted shape or 3D profile. More particularly, during the generation of 3D package profiles in accordance with embodiments of the present disclosure, the package is not subjected to package-external forces that may significantly alter or change the true surface topology of the package (e.g., as a result of compression-induced package deformation or distortion that can occur when the package is forced against a planar reference surface), where the true surface topology of the package is defined by the package's freely-resting state.

For instance, an optimal or most correct TPT reading or measurement can be defined as the total package height obtained as a result of imaging the package when the package is not subjected to externally applied stresses or forces other than gravitational forces, and the packaged device remains uncompressed (i.e., no external compression forces are exerted upon the package, other than compression due to gravitational forces that are naturally or intrinsically exerted on the package). A near-optimal, essentially, effectively or nearly equivalent or accurate, highly-acceptable, or next best TPT reading or measurement is the total package height obtained as a result of imaging the package when extrinsic non-gravitational forces applied to the package are carefully controlled, greatly reduced, and/or minimized compared to the conventional approach in which the entirety or essentially the entirety of the area of the top or bottom surface of the package, or large portions (e.g., more than 25%, or more than 50%, or more than 80%) of the area of the top or bottom surface of the package, are intentionally forced or compressed against a planar reference surface, particularly by avoiding the intentional forcing or compression of the package against a planar reference surface during 3D package imaging or scanning operations.

The extent of package surface warpage or distortion or the thickness profile of the overall package in its natural, uncompressed state (e.g., a freely-resting state) or a state that is essentially identical or equivalent to its natural, uncompressed state, for instance, such that overall package deformation is less than or equal to 20% (e.g., less than or equal to 15%, 10%, 5%, 2.5%, or 1%) of the amount of package deformation that would occur in the event that the package was forcibly compressed against a planar reference surface (as is done conventionally, but is not in accordance with various embodiments in accordance with the present disclosure), can provide information about or facilitate or enable the determination of (a) the suitability of the packaged device for downstream mounting in a product such as a mobile device; (b) possible errors or defects in the package; (c) errors in device or overall package design; and/or (d) errors or problems in upstream manufacturing processes involved in or which led to the production of the packaged device.

Embodiments in accordance with the present disclosure include the performance of a first 3D imaging or scanning procedure or process directed to obtaining, generating, or capturing a 3D profile image or dataset of one of the top and bottom surfaces of a package under inspection, and the performance of a second 3D imaging or scanning procedure or process directed to obtaining, generating, or capturing a 3D profile image or dataset of the other of the top and bottom surface of the package under inspection. Embodiments in accordance with the present disclosure also include the performance of a set of sidewall imaging or scanning procedures or processes directed to obtaining, generating, or capturing 2D (and/or possibly 3D profile) images or datasets of at least two sidewalls of the package under inspection.

With respect to imaging or scanning the top and bottom surface profiles of the package, the first 3D imaging or scanning process can be directed to imaging or scanning the top surface of the package, and the second 3D imaging or scanning process can be directed to imaging or scanning the bottom surface of the package. Alternatively, the first 3D imaging or scanning process can be directed to imaging or scanning the bottom surface of the package, and the second 3D imaging or scanning process can be directed to imaging or scanning the top surface of the package. Individuals having ordinary skill in the art will readily understand that the particular package surface (e.g., top or bottom) to which the first 3D scanning process is directed and the particular opposing package surface (e.g., bottom or top) to which the second 3D scanning process is directed can depend upon the type or characteristics of the package under consideration, the selection or definition of which package surface is the top surface and which package surface is the bottom surface, the capabilities or configuration of package handling and/or inspection equipment, and/or specific embodiment or implementation details. For purpose of simplicity, clarity, and to aid understanding, in the description that immediately follows, the first 3D scanning process is defined to be directed to the top surface of the package, and the second 3D scanning process is defined to be directed to the bottom surface of the package.

In view of the foregoing, depending upon embodiment details, the first or top view 3D scanning process can occur while the top surface of the package is exposed and the package is freely at rest upon or against an object support or seating surface or plane, or while the bottom surface of the package is engaged with or held by a suction/vacuum pick-up tip, head, or nozzle (e.g., a conventional pick-and-place suction/vacuum nozzle) that exerts only an amount of suction/vacuum force upon the package that is sufficient to reliably overcome the gravitational force(s) on the package (as can readily be determined by routine experimentation by individuals having ordinary skill in the art for any given type of package), and the total package surface area across which this suction/vacuum force is applied or exerted is typically less than or equal to 5%-50% (e.g., no more than 10%, 15%, 20%, 25%, 30%, 35%, 40%, or 45%) of the area spanned by the top or bottom surface of the package, depending upon the geometry of the package structure, the geometry of the suction/vacuum nozzle, and/or how the package is carried, elevated, or lifted by the suction/vacuum nozzle. Furthermore, the second or bottom view 3D scanning process can occur while the bottom surface of the package is exposed and the top surface of the package is freely at rest upon or against an object support surface or plane, or while the top surface of the package is engaged with or held by a suction/vacuum pick-up tip, head, or nozzle that exerts only an amount of suction/vacuum force upon the package that is sufficient to reliably overcome the gravitational force(s) on the package (as can also readily be determined by routine experimentation by individuals having ordinary skill in the art for any given type of package), and the total package surface area across which this suction/vacuum force is applied or exerted is typically less than or equal to 5%-50% (e.g., no more than 10%, 15%, 20%, 25%, 30%, 35%, 40%, or 45%) of the area spanned by the top or bottom surface of the package, depending upon the geometry of the package, the geometry of the suction/vacuum nozzle, and/or how the package is carried, elevated, or lifted by the suction/vacuum nozzle.

In multiple embodiments, one of the first or top view 3D scanning process and the second or bottom view 3D scanning process is performed upon the package while the package is freely at rest against a support surface or plane; and the other of the first or top view 3D scanning process and the second or bottom view 3D scanning process is performed upon the package while portions of the package are carried by a suction/vacuum nozzle (e.g., in a manner indicated above or elsewhere herein). For instance, the first or top view 3D scanning process can be performed upon the package while the bottom surface of the package is freely at rest against a support surface or plane; and the second or bottom view 3D scanning process can be performed upon the package while portions of the top surface package is carried by a suction/vacuum nozzle as indicated above.

In some embodiments, each of the top view 3D scanning process and the bottom view 3D scanning process is performed while the package is freely at rest against a support surface or plane. Depending upon embodiment details, when each of the top view 3D scanning process and the bottom view 3D scanning process are performed while the package is freely resting against a support surface or plane, the top view 3D scanning process can occur while the package naturally or freely rests on a first seating surface or plane, and the bottom view 3D scanning process can occur while the package naturally or freely rests on this same or a different seating surface or plane (e.g., a distinct second seating plane).

In specific embodiments, the top view 3D scanning process can be performed by generating or capturing a 3D profile of the top surface of the package from above while the top surface of the package is exposed and lower or lowest portions of the package freely rest on or against a support surface or plane, where the support surface is provided by a portion, section, or compartment of a carrier such as a tray, boat, or another type of platform, substrate, or medium on or in which the packaged semiconductor device is stored and/or transported (e.g., a tape or tape structure having pockets into which packaged semiconductor devices can be loaded, such as by way of a tape and reel machine). The bottom view 3D scanning process can be performed, for instance, by generating or capturing a 3D profile of the bottom surface of the package either before (e.g., just prior to) or during the loading the package onto or into the carrier.

Alternatively, the bottom view 3D scanning process can be performed while the top surface of the package is exposed and lower or lowest portions of the package freely rest on or against the support surface or plane, provided that the support surface or plane (e.g., formed by bottom, base, or underside portions of a carrier such as indicated above) is optically transparent or translucent with respect to the optical wavelengths used to generate or capture the 3D profile of the bottom surface of the package during the bottom view 3D scanning process. In various embodiments, the top view 3D scanning process and the bottom view 3D scanning process directed to a given package occur separately or sequentially in time. However, in embodiments in which the support surface or plane is optically transparent or translucent with respect to the optical wavelengths used to generate or capture 3D profiles, the top view 3D scanning process and the bottom view 3D scanning process can occur simultaneously. A mathematical correction factor can be applied to an imaging dataset to account for index of refraction effects when imaging or scanning occurs through a substance or medium other than air or vacuum, in a manner readily understood by individuals having ordinary skill in the relevant art, such that measurement values determined from the imaging dataset (e.g., TMT values and/or TPT values) are appropriately or accurately scaled or corrected.

Still further alternatively, the top view 3D scanning process and the bottom view 3D scanning process can be performed sequentially or simultaneously in embodiments in which the package is retained, held, or supported at or along particular points or portions of its edges or periphery in a manner that avoids or essentially avoids the application of compressive force(s) to the package other than natural gravitational force(s), for instance, when a set of peripheral points or segments of the package along at least three lower peripheral edges or borders of the package are supported by projections such as pins.

In view of the foregoing, multiple embodiment variations in accordance with the present disclosure exist. Notwithstanding, a key aspect of each embodiment is the reduction, minimization, or elimination of package distortion or warpage during 3D imaging or scanning due to forces other than or apart from the natural force(s) of gravity that normally act on the package while the package is freely at rest, especially by way of avoiding the application of external non-gravitational compressive forces to the package or significant portions of the top or bottom package surface areas that force, press, or push the package against a planar reference surface. A further key aspect is the generation or capture of package sidewall images (e.g., at least two package sidewall images), as described in detail below; and yet another key aspect is the generation of a synthesized, calculated, combined, or composite 3D image in which the top view 3D profile of the package, the bottom view 3D profile of the package, and the package sidewall images are unified, united, assembled, or joined or stitched together, as also described in detail below. An additional key aspect is the estimation of determination of 3D package characteristics or parameters based on the composite 3D image.

For purpose of simplicity, clarity, and to aid understanding, in the description that immediately follows, a representative embodiment (e.g., a first representative embodiment) is considered in which each of the top view 3D scanning process and the bottom view 3D scanning process are performed while the package is freely at rest against an object or package seating plane. Thus, in this representative embodiment, the top view 3D scanning process can be defined as a resting top view 3D scanning process, and the bottom view 3D scanning process can be defined as a resting bottom view 3D scanning process.

During the resting top view 3D scanning process, lower-most portions of an object under consideration (e.g., a package as described above) freely or naturally rest on an object support, sitting, or seating plane, in the absence of the application of externally-applied suction or compression forces to the object (other than the naturally occurring force of gravity acting upon the object as lower-most portions of the object freely rest on the seating plane). Consequently, the object is not physically deformed as a result of being subjected to forced compression against an object-external reference plane. The resting top view 3D scanning process can involve or include generating a top view 3D profile of the overall object, for instance, by way of a conventional first scan line or thin line illumination procedure and the conventional capture of scan line illumination reflected from the object (e.g., using a conventional 3D profile camera setup), in a manner readily understood by individuals having ordinary skill in the relevant art. Such a top view 3D scanning process results in the generation of a top view 3D scan line dataset representing the 3D profile of the overall object from an angled top view or a top perspective view.

During the resting bottom view 3D scanning process, upper-most portions of the object freely or naturally rest on the same or another object support, sitting, or seating plane, without the application of external suction or compression forces to the object (other than the naturally occurring force of gravity acting upon the object as upper-most portions of the object freely rest on the seating plane). Consequently, the object is not physically deformed as a result of being subjected to forced compression against a component-external reference plane. The resting bottom view 3D scanning process can involve or include generating a bottom view 3D profile of the overall object, for instance, by way of a conventional second scan line or thin line illumination procedure and the conventional capture of scan line illumination reflected from the object (e.g., using a conventional 3D profile camera setup), in a manner readily understood by individuals having ordinary skill in the relevant art. Such a bottom view 3D scanning process results in the generation of a bottom view 3D scan line dataset representing the 3D profile of the overall object from an angled bottom view or a bottom perspective view.

Individuals having ordinary skill in the art will further recognize that in various embodiments, during the top view 3D scanning process if structures or portions of the object exist that project outward from the top surface of the object along the z-axis in a common direction away from each of the top surface of the object and the bottom surface of the object, such structures or portions of the object can or will be at least partially imaged and captured in the top view 3D scan line dataset; and/or portions of one or more object sidewalls that extend along the z-axis away from the top surface of the object toward the bottom surface of the object can or will be at least partially imaged or captured in the top view 3D scan line dataset. Analogously, during the bottom view 3D scanning process, if structures or portions of the object exist that project outward from the bottom surface of the object along the z-axis in a common direction away from each of the bottom surface of the object and the top surface of the object, such structures or portions of the object can be at least partially imaged and captured in the bottom view 3D scan line dataset; and/or portions of one or more object sidewalls that extend downward away from the top surface toward the bottom surface of the object can be at least partially imaged or captured in the bottom view 3D scan line dataset.

As indicated above, in the event that the object under consideration is a packaged semiconductor device (e.g., a molded package containing one or more semiconductor die or integrated circuit chips), the seating plane can be a portion or pocket of a tray (e.g., a JEDEC tray), boat, or other type of platform, substrate, or medium (e.g., a conventional or semiconductor industry standard/standardized platform, substrate, or medium) on or in which the packaged semiconductor device is stored and/or transported (e.g., a tape having pockets into which packaged semiconductor devices can be loaded, such as by way of a tape and reel machine). In such a situation, lower-most portions of the packaged semiconductor device that rest against the seating plane during the top view 3D scanning process can be solder bumps or electrical contact pads that project outward from or beyond the bottom surface or underside of the molded packaged toward and/or to the seating plane. Moreover, upper-most portions of the packaged semiconductor device that rest against the seating plane during the bottom view 3D scanning process can be portions of the top or upper surface of the molded package.

Embodiments in accordance with the present disclosure additionally or alternatively include (a) generating a 3D synthesized, combined, or composite image of an object under consideration, or equivalently, generating a 3D composite image dataset for the object; and (b) determining object characteristics or properties, inspecting the object, and/or estimating or evaluating object suitability and/or reliability for particular purposes or environments (e.g., product environments) based on the generated 3D composite image or 3D composite image dataset.

In several embodiments, a process for generating a 3D composite image or image dataset of an object includes (i) a top surface of curvature image or image dataset generation procedure; (ii) a bottom surface of curvature image or image dataset generation procedure; (iii) a sidewall image capture or image dataset generation procedure; and (iv) a 3D composite image assembly procedure.

In multiple embodiments, the top surface of curvature image or image dataset generation procedure includes: performing a top surface 3D imaging procedure including providing or generating a 3D profile such as a 3D scan line or thin line profile (e.g., a conventional 3D scan line profile) of the physical top surface of the object by way of using scan line or thin line illumination (e.g., while portions of the bottom or bottom surface of the object naturally or freely rest upon a reference or seating plane and are retained thereon by gravitational force, in the absence of the further application of compressive or suction forces to the object), to thereby provide or produce a top surface 3D profile or 3D scan line profile dataset; deriving, determining or calculating a reference, best-fit, or normalized top surface plane, plane shape, or planar shape (for instance, a linear regression plane, plane shape, or planar shape in an embodiment, e.g., which can correspond to or defines a regular geometric shape or polygon such as a rectangle) defined by an array of (x, y) points corresponding to or through the top surface 3D profile or 3D scan line profile; and numerically or digitally mapping, determining, or calculating z-axis deviations of the top surface 3D profile or 3D scan line profile relative to or away from this top surface best-fit plane at each point across the array of (x, y) points defining the top surface best-fit plane to produce or numerically yield a top surface of curvature image or image dataset, which is represented, defined, or stored as an array of (x, y, z) values (e.g., a first array of (x, y, z) values). Any given (x, y, z) value of the top surface of curvature image or image dataset defines a set of pixel space (x, y, z) coordinates in which the z coordinate value corresponds to, establishes, or defines a relative or normalized z-axis deviation of the top surface 3D profile or 3D scan line profile away from the top surface best-fit plane at a particular pixel space (x, y) point of the top surface best-fit plane.

The aforementioned top surface of curvature image or image data set corresponds to, can be used to generate, or forms a top surface profile (TSP) dataset for the object. More particularly, the array of top surface of curvature image or image dataset (x, y) values can be used to generate, establish, or provide an array of TSP(x, y) values, where such TSP(x, y) values represent z-axis deviations between the top surface of the object and the reference, normalized, or best-fit object top surface plane. Thus, the TSP(x, y) values correspond to or are numerically correlated with changes in the top surface topography or contour of the object relative to the reference, normalized, or best-fit object top surface plane. The array of TWP(x, y) values therefore estimates or indicates on an (x, y) point relative basis topographic, z-axis, or height-wise variations across the top surface of the object, e.g., corresponding to object top surface height non-uniformity, distortion(s), for instance, arising from object stresses or warpage.

Depending upon embodiment details, the top surface best-fit plane, plane shape, or planar shape can be numerically generated or defined to have lateral or outermost boundaries, borders, or edges corresponding to the as-manufactured physical lateral or outermost boundaries, borders, or edges of the top surface of the packaged composite device, but which are shifted, offset, or disposed in pixel space by a selectable/selected, programmable, or predetermined number of pixels inward toward the midpoint or centroid of the top surface of the packaged composite device. An individual having ordinary skill in the relevant art will understand that such an inward pixel space shift or offset of the lateral or outermost borders or edges of the top surface best-fit plane (a) will map, convert to, or represent a selectable/selected, programmable, or predetermined physical space distance, such as a particular number of microns, away from the actual lateral or outermost borders or edges of the top surface of the as-manufactured packaged composite device; and (b) can aid in excluding physical irregularities in one or more of the as-manufactured packaged composite device's top surface lateral or outermost borders or edges from leading to irregularities in the lateral or outermost borders or edges of the top surface best-fit plane.

In various embodiments, if the top surface of the object carries structures that project outward from the top surface of the object along the z-axis and which should not themselves be considered as forming or belonging to the top surface of the object, the top surface of curvature image or image dataset generation procedure can include a top surface estimation procedure by which such structures are numerically excluded or removed from the top surface of curvature image or image dataset, in a manner readily understood by individuals having ordinary skill in the relevant art.

In a manner analogous to the foregoing, in multiple embodiments the bottom surface of curvature image or image dataset generation procedure includes: performing a bottom surface 3D imaging procedure including providing or generating a 3D profile such as a 3D scan line or thin line profile (e.g., a conventional 3D scan line profile) of the physical bottom surface of the object by way of using scan line or thin line illumination (e.g., while portions of the top or top surface of the object freely rest upon the reference or seating plane and are retained thereon by gravitational force, in the absence of the further application of compressive or suction forces to the object), to thereby provide or produce a bottom surface 3D profile or 3D scan line profile dataset; deriving, determining, or calculating a reference, best-fit, or normalized bottom surface plane, plane shape, or planar shape (for instance, a linear regression plane, plane shape, or planar shape in an embodiment, e.g., which corresponds to or defines a regular geometric shape or polygon such as a rectangle) defined by an array of (x, y) points corresponding to or through the bottom surface 3D profile or 3D scan line profile; and numerically or digitally mapping, determining, or calculating z-axis deviations of the bottom surface 3D profile or 3D scan line profile relative to or away from this bottom surface best-fit plane at each point across the array of (x, y) points defining the bottom surface best-fit plane to produce or numerically yield a bottom surface of curvature image or image dataset, which is represented, defined, or stored as an array of (x, y, z) values (e.g., a second array of (x, y, z) values). Any given (x, y, z) value of the bottom surface of curvature image or image dataset defines a set of pixel space (x, y, z) coordinates in which the z coordinate value corresponds to, establishes, or defines a relative or normalized z-axis deviation of the bottom surface 3D profile or 3D scan line profile away from the bottom surface best-fit plane at a particular pixel space (x, y) point of the bottom surface best-fit plane.

The aforementioned bottom surface of curvature image or image data set corresponds to, can be used to generate, or forms a bottom surface profile (BSP) dataset for the object. More particularly, the array of bottom surface of curvature image or image dataset (x, y) values can be used to generate, establish, or provide an array of BSP(x, y) values, where such BSP(x, y) values represent z-axis deviations between the bottom surface of the object and the reference, normalized, or best-fit object top surface plane. Thus, the BSP(x, y) values correspond to or are numerically correlated with changes in the bottom surface topography or contour of the object relative to the reference, normalized, or best-fit object bottom surface plane. The array of BWP(x, y) values therefore estimates or indicates on an (x, y) point relative basis topographic, z-axis, or height-wise variations across the bottom surface of the object, e.g., corresponding to object bottom surface height non-uniformity, distortion(s), for instance, arising from object stresses or warpage.

Depending upon embodiment details, the bottom surface best-fit plane, plane shape, or planar shape can be numerically generated or defined to have lateral or outermost boundaries, borders, or edges corresponding to the as-manufactured physical lateral or outermost boundaries, borders, or edges of the bottom surface of the packaged composite device, but which are shifted, offset, or disposed in pixel space by a selectable/selected, programmable, or predetermined number of pixels inward toward the midpoint or centroid of the bottom surface of the packaged composite device. An individual having ordinary skill in the relevant art will understand that such an inward pixel space shift or offset of the lateral or outermost borders or edges of the bottom surface best-fit plane (a) will map, convert to, or represent a selectable/selected, programmable, or predetermined physical space distance, such as a particular number of microns, away from the actual lateral or outermost borders or edges of the bottom surface of the as-manufactured packaged composite device; and (b) can aid in excluding physical irregularities in one or more of the as-manufactured packaged composite device's bottom surface lateral or outermost borders or edges from leading to irregularities in the lateral or outermost borders or edges of the bottom surface best-fit plane.

In various embodiments, if the bottom surface of the object carries structures that project outward from the bottom surface of the object along the z-axis and which may or should not themselves be considered as forming or belonging to the bottom surface of the object (e.g., solder bumps or electrical contact pads), the bottom surface of curvature image or image dataset generation procedure can include a bottom surface estimation procedure by which such structures are numerically excluded or removed from the bottom surface of curvature image or image dataset, in a manner readily understood by individuals having ordinary skill in the relevant art.

The object periphery or sidewall image capture procedure includes providing, capturing, or generating a 2D image or image dataset for each of at least two object sidewalls, e.g., at least two opposing object sidewalls, i.e., generating 2D images or image datasets for a plurality of object sidewalls, such as at least two opposing object sidewalls. In several embodiments, for an object having four sidewalls, the sidewall image capture procedure includes capturing a 2D image or image dataset of each of the object's four sidewalls. The capture of multiple object sidewalls (e.g., four object sidewalls) can be performed simultaneously by way of a conventional multi-side object imaging/image capture/inspection apparatus or system, in a manner readily understood by individuals having ordinary skill in the relevant art.

The 3D composite image assembly procedure includes digitally referencing, aligning, and uniting, and joining at least corner portions or points, and/or possibly one or more outer edge or border portion or sections, in each of (a) the top surface of curvature image or image dataset or TSP(x, y) dataset and (b) the bottom surface of curvature image or image dataset or BSP(x, y) dataset with corresponding corner, edge, border, or z-axis extremity portions or points in at least two or each of the plurality of captured 2D sidewall images or image datasets; and storing the united or joined (i) top surface of curvature image or image dataset or TSP(x, y) dataset, (ii) bottom surface of curvature image or image dataset or BSP(x, y) dataset, and (iii) sidewall images or image dataset as the 3D composite image or image dataset (e.g., a single 3D composite image or image dataset).

As will be readily understood by individuals having ordinary skill in the relevant art, in the 3D composite image or image dataset, the size or dimensions of each pixel in pixel space corresponds to and can be referenced, mapped, or converted to the size or dimensions of a known physical area in real space. Furthermore, individuals having ordinary skill in the relevant art will thoroughly understand how pixel space dimensions can be mapped or converted to physical or real space dimensions, taking into account optical system magnification and image sensor resolution. Individuals having ordinary skill in the art will additionally understand that in various embodiments, the sizes or dimensions of each pixel in the top surface of curvature image or image dataset, the bottom surface of curvature image or image dataset, and each sidewall image or image dataset can be established to be equal to each other, or appropriately scaled relative to each other prior to or in association with unifying or joining the top surface of curvature image or image dataset, the bottom surface of curvature image or image dataset, and the sidewall images or image datasets together to form the 3D composite image or image dataset in order to facilitate ease of 3D composite image or image dataset pixel space to physical space dimension mapping or conversion.

Moreover, the pixel space extent, area, or aspect ratio of the top surface of curvature image or image dataset and the pixel space extent, area, or aspect ratio of the bottom surface of curvature image or image dataset can be scaled relative to the pixel space positions or locations of the 2D sidewall images prior to or in association with forming the 3D composite image, such that corner portions or points of the top surface of curvature image or image dataset and the bottom surface of curvature image or image dataset can be aligned or registered relative to and linked, unified, mated, merged, or joined with counterpart corner or edge portions or points of the 2D sidewall images or image datasets. Thus, the (x, y) aspect ratios, established in a first pixel space, of each of the top surface of curvature image or image dataset and the bottom surface of curvature image or image dataset, which correspond to the physical space dimensions of the object from a top view and a bottom view, respectively, can be scaled as needed relative to the (x, y) positions or coordinates, established in a second pixel space that is distinct or distinguishable from the first pixel space, of the plurality of 2D sidewall images or image datasets. Moreover, an as-captured (x, y) aspect ratio of the top surface of curvature image or image dataset established in accordance with a top surface pixel space and/or an as-captured (x, y) aspect ratio of the bottom surface of curvature image or image dataset established in accordance with a bottom surface pixel space, which can be identical to or different than the top surface pixel space, can be scaled to align, mate, or match with the (x, y) locations or positions of the 2D sidewall images established in accordance with a sidewall image pixel space, in a manner readily understood by an individual having ordinary skill in the relevant art.

In view of the foregoing, embodiments in accordance with the present disclosure can additionally generate or determine an (x, y) array of object main body z-axis readings, measurements, or thickness values across at least portions of the object's (x, y) extent or surface area, where such (x, y) object main body thickness values correspond to, estimate, or indicate the thickness of the object's main body, exclusive of structures (e.g., solder balls) carried by the object's main body that project in z-axis directions, at specific (x, y) points. More particularly, based on or using the 3D composite image dataset, various embodiments in accordance with the present disclosure determine or generate an (x, y) array of True Object Main Body Thickness (TOMBT) values, i.e., an array of TOMBT(x, y) values such as TMT(x, y) values, where any given TOMBT(x, y) value or TMT(x, y) value is a number that represents the z-axis distance or separation (in pixel space or as mapped to or calculated for physical/real space) between the TSP and the BSP within the 3D composite image at that specific (x, y) point. Once the 3D composite image has been generated, TOMBT(x, y) or TMT(x, y) values can be determined by way of subtraction operations, in a manner readily understood by individuals having ordinary skill in the relevant art.

Various embodiments of an inspection process in accordance with the present disclosure further include estimating, determining, or measuring a set of object characteristics, properties, or parameters based on or using the 3D composite image or image dataset, the array of TMT(x, y) values, and/or other information generated or determined by way of the object imaging or scanning procedures. Such object characteristics or properties can include a maximum object body thickness (TMT max), and/or a minimum object body thickness (TMT min) between the object top surface and object bottom surface; and/or one or more measures of or numerically derived (e.g., curve-fit) mathematical functions representing object z-axis contour(s), bulge(s) and/or thinning between one or more sidewalls or along particular object sidewalls; and/or other object properties.

As indicated above for the top view 3D scanning process and the bottom view 3D scanning process, during scan line image capture procedures corresponding to the generation of the 3D scan line profile of the top surface of the object and the generation of the 3D scan line profile of the bottom surface of the object, in at least some representative embodiments (e.g., the aforementioned first representative embodiment), the object is freely or naturally resting on a seating plane with its top surface exposed or its bottom surface exposed, respectively. For instance, if the object is a packaged semiconductor component, the object can rest in or on a standard tray (e.g., a JEDEC tray), boat, or tape in association with the generation of the 3D scan line profiles of the top and/or bottom object surfaces of the component. Consequently, during the generation of the 3D scan line profiles of the component top and bottom surfaces, the component is not physically distorted or deformed as a result of being held by a suction nozzle and/or subjected to forced compression against a component-external reference plane. Therefore, a 3D composite image or image dataset generated in accordance with an embodiment of the present disclosure provides an accurate or much more accurate 3D representation of the component compared to prior 3D object inspection techniques in which a potentially deformable object is subjected to undesirable externally applied forces or stresses during image capture operations.

In other embodiments, one or each of the top view 3D imaging or scanning process and the bottom view 3D imaging or scanning process can occur while a portion of the area (e.g., less than or equal to 10%-50%, as set forth above) of bottom or top surface, respectively, of the package is held or carried by a pick-up device such as a suction/vacuum nozzle. In such embodiments, the generation of each image and image dataset described above, and the operations performed in order to generate and analyse or evaluate the 3D composite image dataset are identical, essentially identical, or analogous manner to those described above.

In addition to the foregoing, in accordance with embodiments of the present disclosure, no object-external or object-extrinsic reference datum is needed or utilized in association with generating the 3D composite image or image dataset, as accurate object measurements can be derived or obtained from the 3D composite image or image dataset without the need for referencing any portion of the object to an object-external datum. If desired or required, an object-based, object-intrinsic/object-internal, or object reference surface datum can be numerically derived or generated from the 3D composite image or image dataset.

Still further to the foregoing, with respect to the 3D inspection of a series or sequence of multiple objects (e.g., in a high-speed or high-throughput manufacturing environment), in some embodiments one or more of the top view 3D scanning process; the bottom view 3D scanning process, the top surface of curvature image or image dataset generation procedure; the bottom surface of curvature image or image dataset generation procedure; the sidewall image capture or image dataset generation procedure; the 3D composite image assembly procedure; and object characterization or evaluation processes (e.g., object pass/fail designation) based on the 3D composite image can occur (a) on-the-fly, e.g., while the multiple objects are in motion, and/or (b) at distinct, segregated, or separate processing stations through which the objects can be transported or transferred.

FIGS. 1-11 are described hereafter to further aid understanding of particular aspects of embodiments in accordance with the present disclosure.

FIG. 1 illustrates particular representative packaged object parameters corresponding to semiconductor devices that reside in a molded package, such as integrated circuit devices or chips that are coated or surrounded by or which are contained or encapsulated within a package made of one or more types of polymer mold materials or compounds (e.g., packaged composite devices), including Total Package Thickness (TPT) and Total Mold Thickness (TMT) parameters, which can be estimated, determined, calculated, or measured in accordance with various embodiments of the present disclosure. Representative orthogonal (x, y, z) axes are also shown in FIG. 1, where z-axis distances are defined to correspond to package height or thickness, and x and y axes correspond to package length and width or a set of planes that contains at least portions of the cross-sectional are of the top package surface and the bottom package surface, in a manner readily understood by individuals having ordinary skill in the relevant art.

In general, a TMT parameter estimates, indicates, or measures an actual vertical or z-axis thickness of polymer mold compound(s) disposed around the semiconductor device(s) or within which the semiconductor device(s) reside, exclusive of solder balls or other types of structures that vertically project away from the top and bottom surfaces of the mold compound. More particularly, as indicated in FIG. 1 in various embodiments, for a given package a maximum TMT (TMT max) can be defined as a maximum mold compound thickness across the (x, y) extent, span, or area the package, e.g., a maximum thickness of packaging material or mold compound(s) across the length and width of the package (which correspond to, are parallel to, or reside in an (x, y) plane), exclusive of solder balls and other types of non-packaging material projections that extend away from the top and bottom surfaces of the package in vertical or z-axis directions. Similarly, a minimum TMT (TMT min) can be defined as a minimum mold compound thickness across the (x, y) extent, span, or area the package, e.g., a minimum thickness of packaging material or mold compound(s) across the length and width of the package, exclusive of solder balls and other types of non-packaging material projections that extend away from the top and bottom surfaces of the package in vertical or z-axis directions.

Moreover, individuals having ordinary skill in the relevant art will readily understand that a True Mold Thickness (x, y) profile or an array of TMT(x, y) values corresponding to or across the (x, y) area of the package can be defined, estimated, calculated, or measured in accordance with embodiments of the present disclosure, which indicates thickness values or relative thickness values of the package mold compound(s) at multiple or many (e.g., several, tens, hundreds, or thousands) of (x, y) coordinates or points across at least portions of the (x, y) extent, span, or surface area of the package, and/or vertical or z-axis variations in the package mold compound(s) thickness between the maximum TMT (TMT max) and the minimum TMT (TMT min) at such (x, y) coordinates or points.

A TPT for the package can be defined as a maximum vertical or z-axis distance or span between a lower-most point on a solder ball or other type of non-packaging material structure that is carried by or which projects away from the package (e.g., which extends below the bottom surface of the package), and a highest point formed by the package mold compound(s) on the opposite surface of the package, across the (x, y) extent, span, or surface area of the package. Thus, the package TPT can be defined as the greatest or largest distance between the bottom of a solder ball (or other type of structure that vertically projects away from the bottom surface of the package mold compound(s)) and the top surface of the package mold compound(s) across the length and width of the package. Such a solder ball can touch or rest against a package sitting or seating plane, but need not necessarily do so depending upon the as-manufactured 3D profile of the package mold compound(s) and the solder balls (or other types of vertical projections as the case may be) that are carried thereby.

Figure 2A:
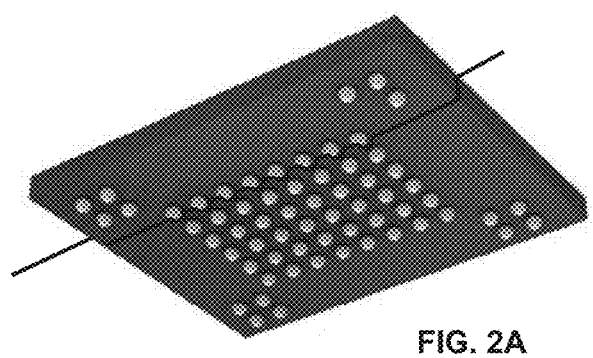
FIGS. 2A-2C show representative images illustrating aspects of scan line or thin line imaging of representative bottom surfaces of packaged devices for generating 3D profile images or image data sets of such package bottom surfaces (e.g., 3D scan line data sets, in a manner that will be readily understood by individuals having ordinary skill in the relevant art.
Figure 2B:
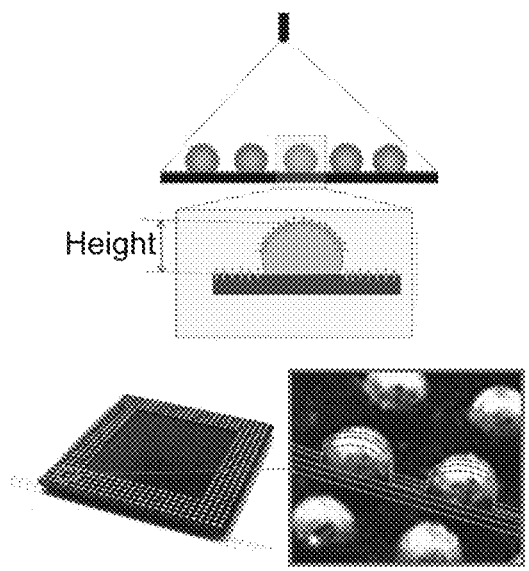
Figure 2C:
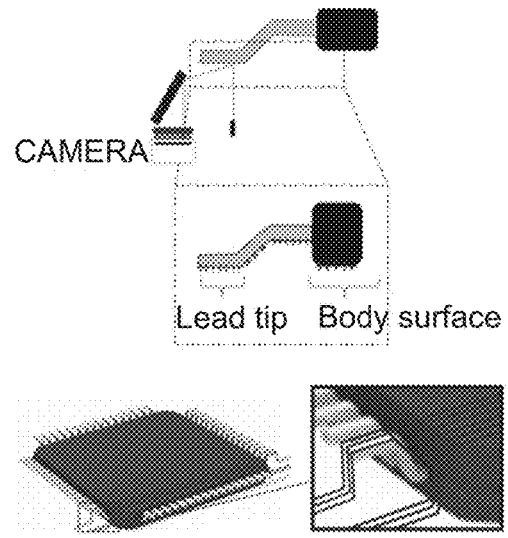

As indicated above, scan line or thin line imaging can be used in association with 3D profile inspection of objects such as packaged semiconductor devices in accordance with at least some embodiments of the present disclosure. FIGS. 2A-2C provide representative images illustrating aspects of scan line or thin line imaging of representative bottom surfaces of packaged devices for generating 3D profile images or image data sets of such package bottom surfaces (e.g., 3D scan line data sets), in a manner that will be readily understood by individuals having ordinary skill in the relevant art. Scan line or thin line imaging can occur in a conventional manner in various embodiments, as individuals having ordinary skill in the relevant art will clearly understand from FIGS. 2A-2C. In representative embodiments or implementations, the thickness of a given illumination scan line can be between 10-20 micrometers (e.g., 15 micrometers), although other (e.g., wider or narrower) illumination line widths can be employed, as will also be readily understood by individuals having ordinary skill in the relevant art. Moreover, a conventional 3D profile camera (e.g., which includes, is based upon, or is an area scan camera) can be used in or form a portion of a scan line or thin line illumination and imaging apparatus for generating 3D scan line profile images and 3D scan line profile datasets corresponding thereto, as portions of a system or apparatus for generating 3D composite images of objects and determining object properties, such as TPT and/or TMT properties, parameters, or values, based thereon in accordance with the present disclosure.

Figure 3:
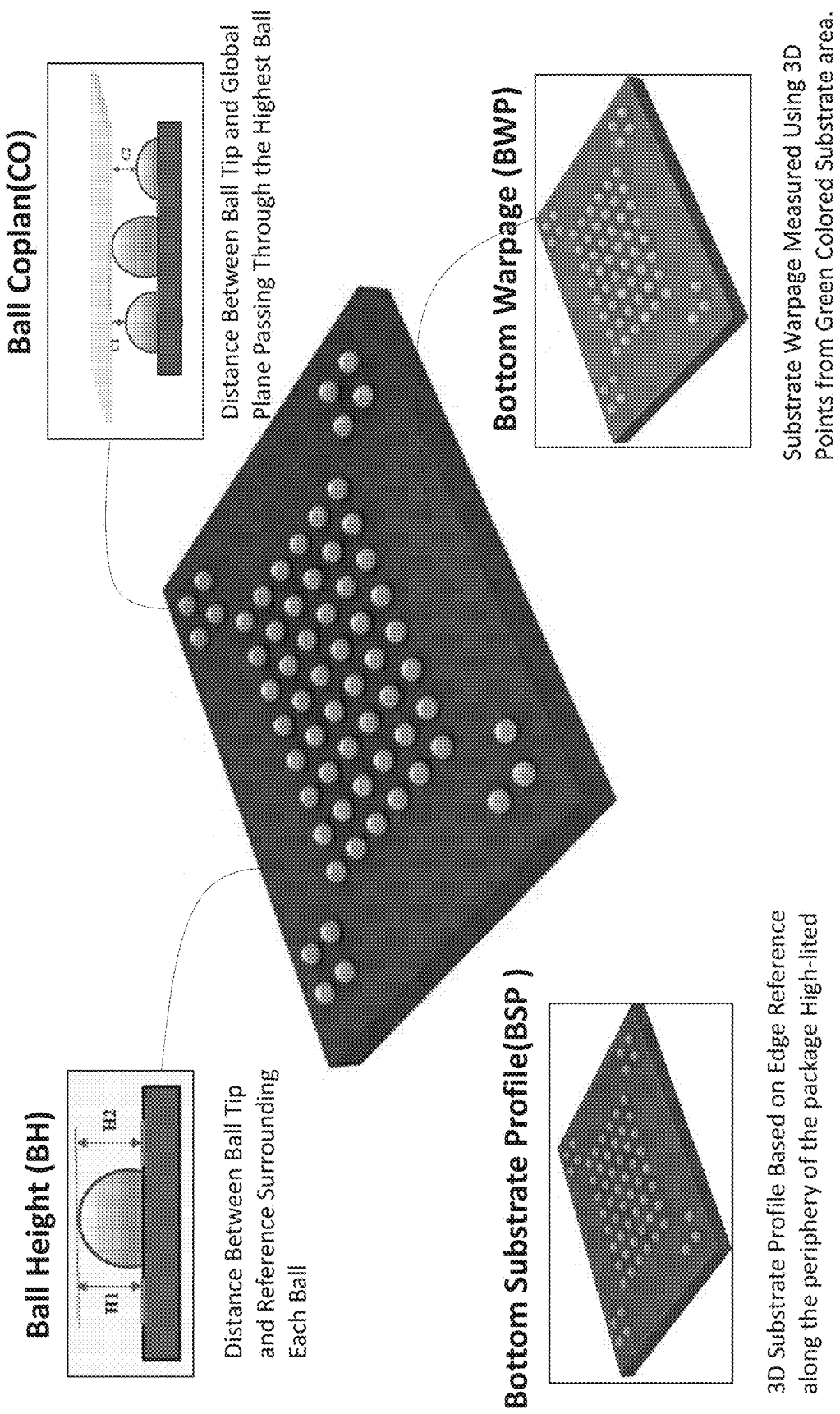
FIG. 3 shows portions of a representative bottom view 3D profile image generated or captured in association with aspects of 3D optical inspection of a packaged semiconductor device, and representative types of information or parameter values that can be determined therefrom in accordance with an embodiment of the present disclosure.

FIG. 3 shows portions of a representative bottom view 3D profile image generated or captured in association with aspects of 3D optical inspection of a packaged semiconductor device, and representative types of information or parameter values that can be determined therefrom in accordance with an embodiment of the present disclosure. As indicated in FIG. 3, from a bottom view 3D scan line profile image, for at least some solder balls, ball height (BH) values can be determined, where any given ball height is defined by a vertical or z-axis distance between the outer surface of the mold compound(s) defining the bottom surface of the package proximate or closest to the solder ball and a peripheral point or tip on the solder ball that is furthest away from this portion of the bottom surface of the package that carries the solder ball.

Additionally, ball coplanarity (CO) values can be determined, wherein for any given solder ball a corresponding coplanarity value is defined by a vertical or z-axis distance between the tip of the solder ball and a global plane for the package that is calculated or defined to touch or pass through the tip of a solder ball having the greatest or highest ball height (BH) value for the package.

Furthermore, an array of BSP(x, y) points corresponding to the bottom surface of the package is determined as indicated above.

Figure 4:
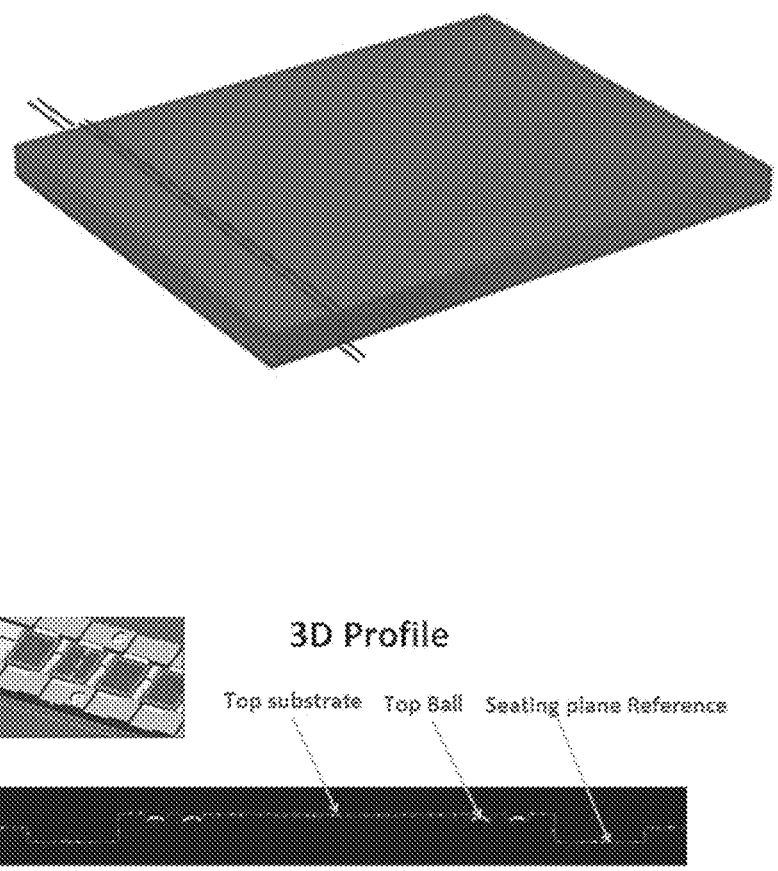
FIG. 4 shows a set of representative top view images illustrating aspects of scan line or thin line imaging of a representative top surface of a packaged semiconductor device and generating a 3D profile image or image dataset corresponding thereto in accordance with an embodiment of the present disclosure.

FIG. 4 shows a set of representative top view images illustrating aspects of scan line or thin line imaging of a representative top surface of a packaged semiconductor device and generating a 3D profile image or image dataset corresponding thereto in accordance with an embodiment of the present disclosure, in a manner that will be readily understood by individuals having ordinary skill in the relevant art. Such scan line or thin line imaging can occur in a conventional manner in various embodiments, as individuals having ordinary skill in the relevant art will clearly understand.

Figure 5:
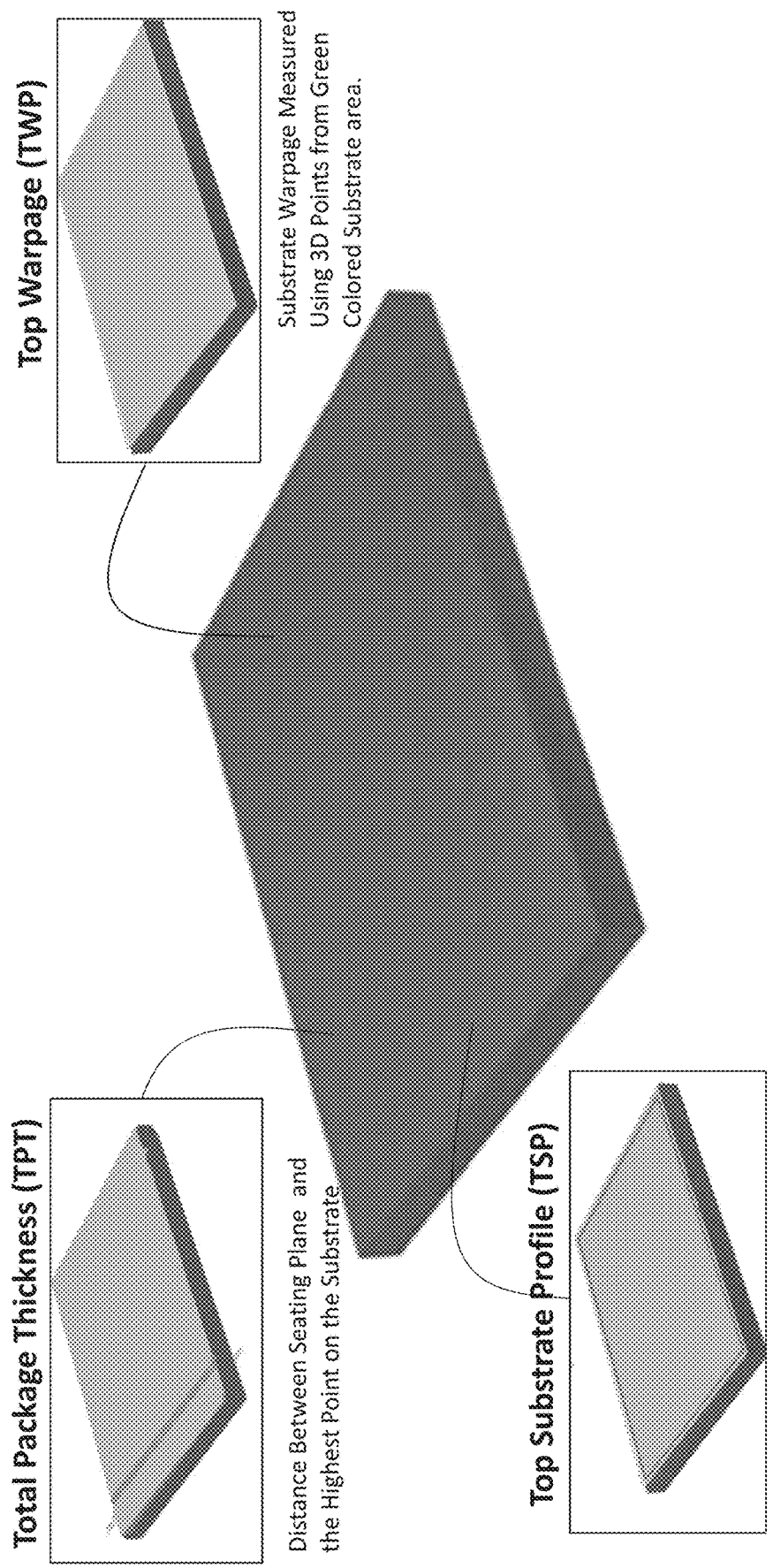
FIG. 5 shows portions of a representative top view image generated or captured in association with aspects of 3D optical inspection of a packaged semiconductor device, and representative types of information or parameter values that can be determined therefrom in accordance with an embodiment of the present disclosure.

FIG. 5 shows a representative top view 3D profile image generated or captured in association with aspects of 3D optical inspection of a packaged semiconductor device, and representative types of information or parameter values that can be determined therefrom in accordance with an embodiment of the present disclosure.

Based on the captured top view 3D profile image, an array of TSP(x, y) points corresponding to the top surface of the package is determined as indicated above. Additionally, a TPT value can be determined based upon the captured top view 3D profile image as a maximum or greatest distance between the upper or upward facing surface of the package sitting or seating plane upon or against which lower or lowest portions of the package rests, and a point on the top surface of the package that is furthest away along the z-axis from or highest relative to this upward facing surface of the package sitting or seating plane.

FIG. 6 indicates a representative plurality of 2D sidewall images captured in association with aspects of optical inspection of a packaged semiconductor device in accordance with an embodiment of the present disclosure. Such 2D sidewall images can correspond to, provide, or define a Side Substrate Profile (SSP) of the packaged semiconductor device. In various embodiments, 2D sidewall images can be captured by an apparatus or system configured for multi-side object, component, or package inspection, such as a conventional or commercially available 4-side or 5-side inspection apparatus, e.g., an apparatus of the type described U.S. Pat. No. 9,816,938, which is incorporated by reference herein in its entirety, or an analogous or similar type of apparatus.

Figure 7A:
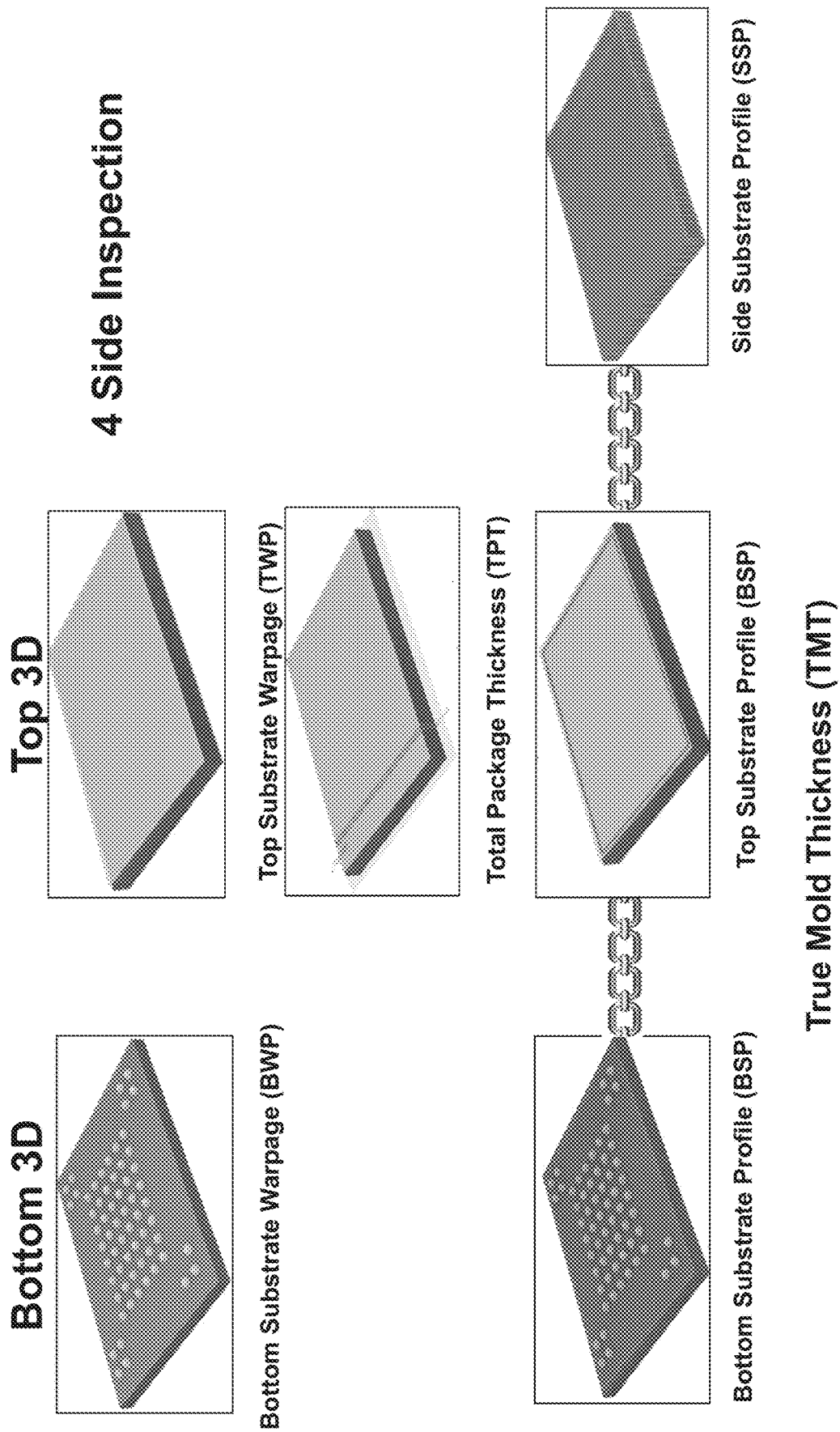
FIG. 7A schematically illustrates the generation of a 3D Bottom Substrate Profile (BSP) and a 3D Top Substrate Profile (TSP) of a packaged semiconductor device, and the combination thereof with a Side Substrate Profile (SSP) formed from a plurality of 2D sidewall images of the packaged semiconductor device to enable the determination of True Mold Thickness (TMT) in accordance with an embodiment of the present disclosure.

FIG. 7A schematically illustrates the generation of particular information, images, or datasets by way of a bottom surface 3D imaging or scanning process, a top surface 3D imaging or scanning process, and a 2D sidewall imaging or scanning process (e.g., a 4 side inspection process) in accordance with an embodiment of the present disclosure. A 3D BSP (e.g., defined by an array of BSP(x, y) values), a 3D TSP (e.g., defined by an array of TSP(x, y) values, and a SSP corresponding to a package can be combined to form a 3D composite image, from which an array of TMT(x, y) values can be determined or calculated as indicated above.

Figure 7B:
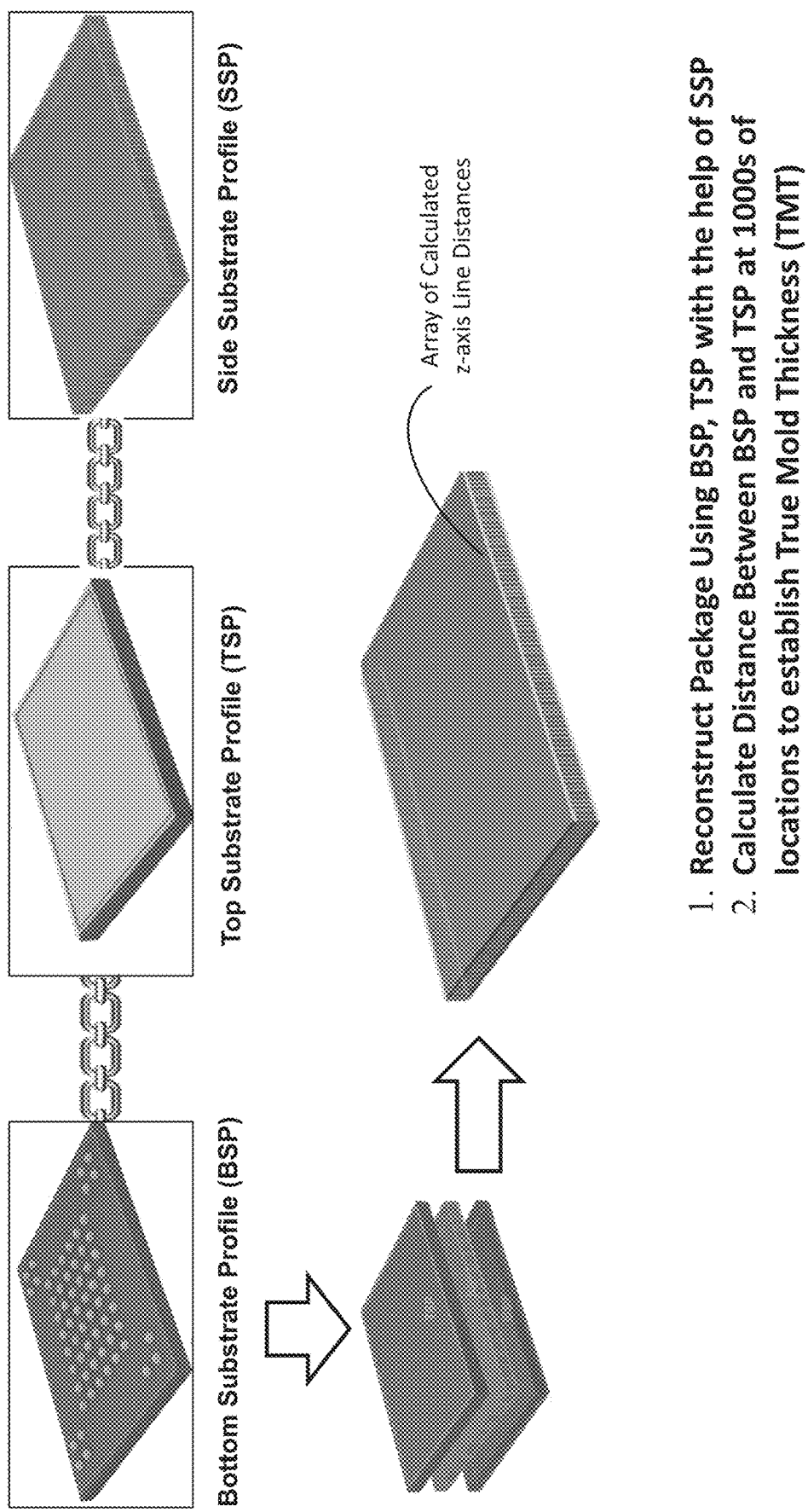
FIG. 7B schematically illustrates further aspects of combining the 3D BSP, the 3D TSP, and a plurality of 2D sidewall images of a packaged semiconductor device to form a 3D composite image of the packaged semiconductor device in accordance with an embodiment of the present disclosure.

FIG. 7B schematically illustrates further aspects of combining the 3D BSP, the 3D TSP, and a plurality of 2D sidewall images as a SSP of a packaged semiconductor device to form a 3D composite image of the packaged semiconductor device(s) in accordance with an embodiment of the present disclosure. The 3D composite image of the packaged semiconductor device(s) is a digital estimation or reconstruction of the actual 3D shape of the physical packaged semiconductor device(s) based on the 3D BSP (x, y values), the 3D TSP (x, y values), and the SSP, in a manner that will be readily understood by individuals having ordinary skill in the relevant art.

Figure 8A:
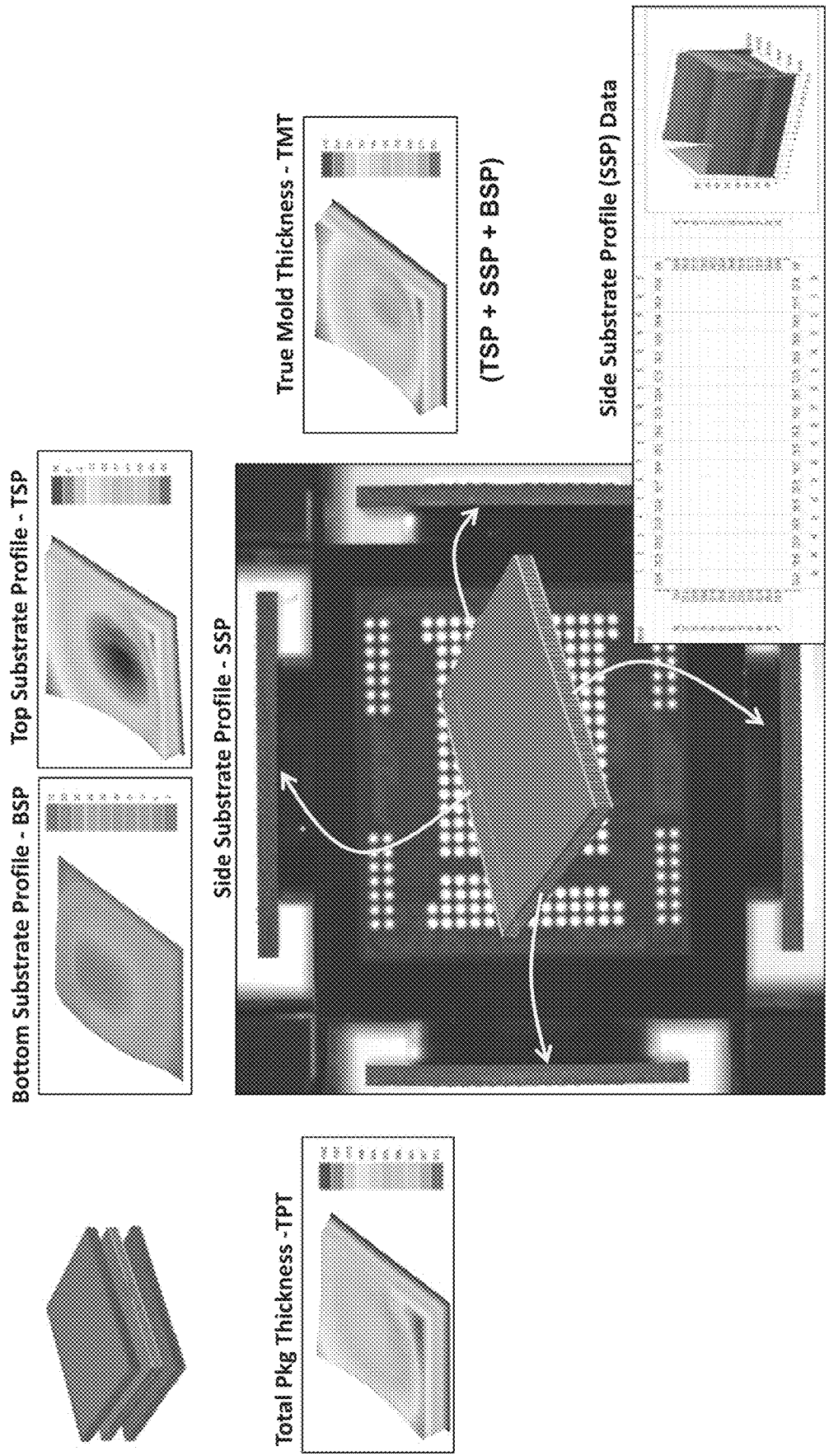
FIG. 8A shows aspects of 3D composite image generation for a representative 11.5 mm×13 mm package in accordance with an embodiment of the present disclosure.
Figure 8B:
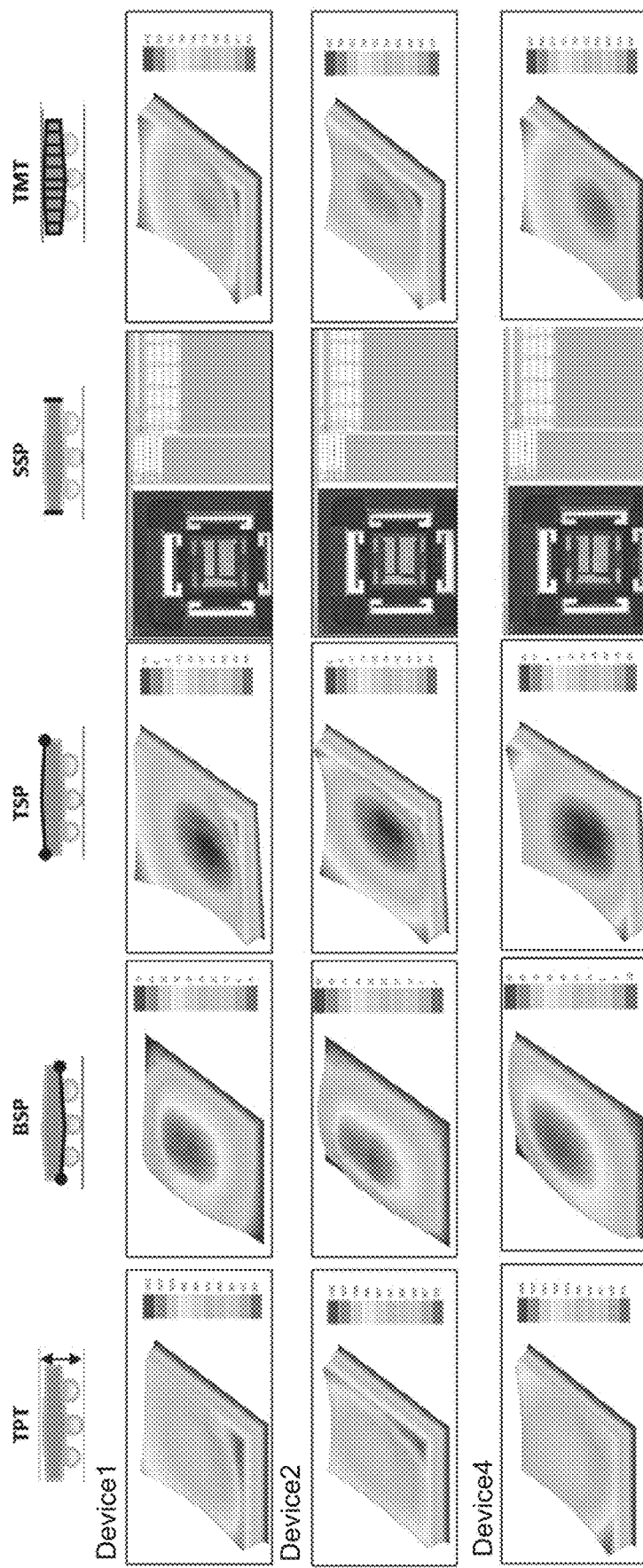
FIG. 8B shows representative scanned images and measurements or evaluation results for three actual 11.5 mm×13 mm devices corresponding to the 3D composite image of the representative 11.5 mm×13 mm package of FIG. 8A.

FIG. 8A shows aspects 3D composite image generation for a representative 11.5 mm×13 mm package in accordance with an embodiment of the present disclosure; and FIG. 8B shows particular representative images and measurements or evaluation results for three actual 11.5 mm×13 mm devices corresponding to the 3D composite image of the representative 11.5 mm×13 mm package of FIG. 8A. FIG. 8C shows particular numerical evaluation or measurement results based on 3D composite images generated in accordance with an embodiment of the present disclosure for seven actual 11.5 mm×13 mm packages.

Figure 9A:
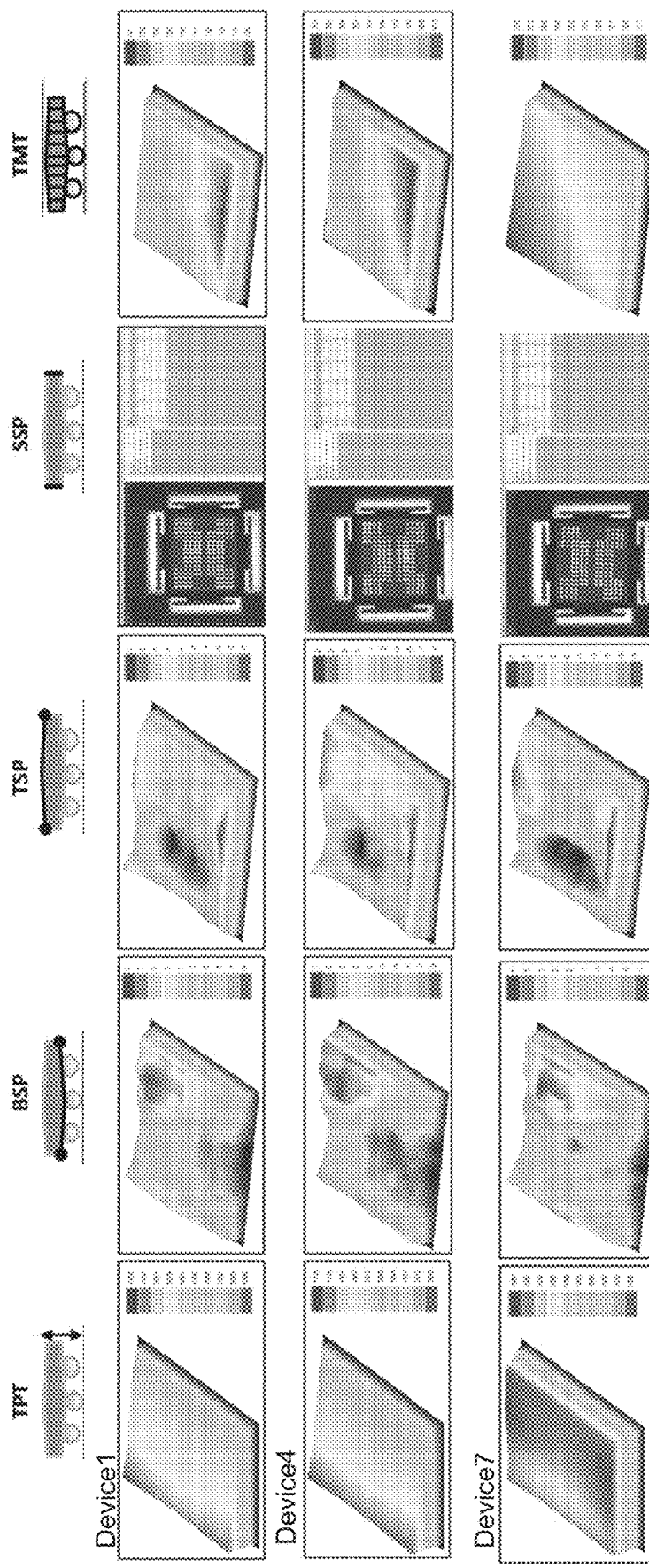
FIG. 9A shows representative types of measurements or evaluation results corresponding to a 3D composite image generated in accordance with an embodiment of the present disclosure for a representative 14 mm×18 mm package.

FIG. 9A shows representative images and measurements or evaluation results corresponding to a 3D composite image generated in accordance with an embodiment of the present disclosure for three actual 14 mm×18 mm packages. FIG. 9B shows representative evaluation or measurement results based on 3D composite images generated in accordance with an embodiment of the present disclosure for seven actual 14 mm×18 mm packages.

FIG. 10 shows measurement comparisons between (a) 3D optical inspection measurements based on 3D composite images generated in accordance with an embodiment of the present disclosure, and (b) measurements made using an optical microscope for reference or "Golden Unit" packages.

With respect to a system, apparatus, or machine for generating 3D composite images of objects and determining object properties, such as TPT and/or TMT properties, parameters, or values, based thereon in accordance with the present disclosure, in various embodiments particular 3D object processing or optical inspection stations, apparatuses, machines, or systems can be configured for performing one or more aspects of 3D object top surface and bottom surface inspection procedures or operations (e.g., one or more portions of the top view 3D scanning process; the bottom view 3D scanning process, the top surface of curvature image or image dataset generation procedure; and/or the bottom surface of curvature image or image dataset generation procedure). Particular 2D (and/or 3D) object processing or optical inspection stations, apparatuses, or systems can also be configured for performing one or more aspects of object sidewall inspection procedures or operations (e.g., portions of the object sidewall scanning process and the generation of object sidewall images or image datasets). Such 3D and 2D object processing or inspection stations, apparatuses, machines, or systems can operate under the control of a set of programmable, specifically programmed, or specifically configured or constructed processing resources, units, or devices (e.g., one or more microprocessors, microcontrollers, specifically configured Field Programmable Gate Arrays (FPGAs) or Programmable Logic Devices (PLDs), and/or state machines), in a manner readily understood by individuals having ordinary skill in the relevant art. Images or image datasets obtained, provided, generated, or captured by a system apparatus, or machine in accordance with an embodiment of the present disclosure can be operated upon by one or more of such types of processing resources. Hence, such types of processing resources can be utilized to operate upon 3D and 2D image datasets to produce 3D composite images in accordance with embodiments of the present disclosure. Images or image datasets provided, produced, obtained, generated, or captured in accordance with embodiments of the present disclosure can reside or be stored in one or more types of computer-readable storage media, such as a set of computer or electronic memories and/or other types of data storage devices (e.g., transistor-based data storage devices, or non-transistor based data storage devices), which can be conventional. Program instruction sets (e.g., software, firmware, microcode) and/or hardware configuration data sets that manage or control the operation of the processing resources that direct the operation of one or more portions of a system or apparatus and/or which generate, analyse, or evaluate 3D composite images in accordance with embodiments of the present disclosure can also reside or be stored in one or types of computer-readable storage media.

Depending upon embodiment details, a system or apparatus in accordance with the present disclosure can be configured for handling, transporting, and/or imaging individual objects or multiple objects disposed in a grouped, gang, or parallel configuration, in a manner readily understood by individuals having ordinary skill in the relevant art.

Figure 11:
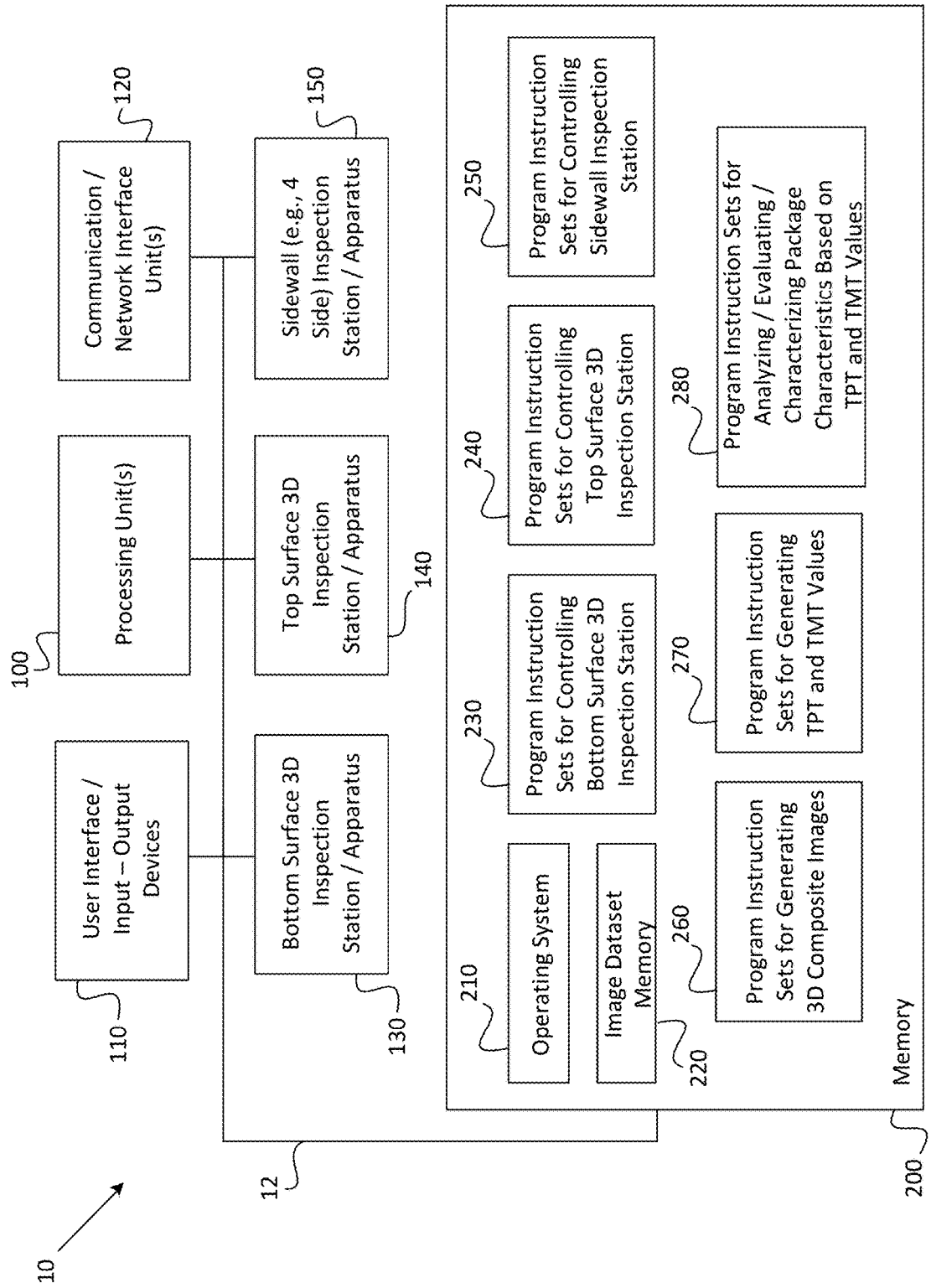
FIG. 11 is a schematic block diagram of an embodiment of a system, apparatus, or machine for generating 3D composite images of objects and determining object properties, such as TPT and/or TMT properties, parameters, or values, based thereon in accordance with an embodiment of the present disclosure.

In a representative embodiment or implementation, a system, apparatus, or machine configured for object inspection in accordance with an embodiment of the present disclosure, which provides 3D and 2D object imaging, scanning, or image capture capabilities and which includes multiple processing stations therein as set forth above is a Hexa or Hexa-based inspection system or machine available from Semiconductor Technologies & Instruments Pte Ltd. (STI), Singapore. FIG. 11 is a schematic block diagram illustration of a system, apparatus, or machine 10 for generating 3D composite images of objects and determining object properties, such as TPT and/or TMT properties, parameters, or values, based thereon in accordance with an embodiment of the present disclosure. In an embodiment, the system 10 includes a set of processing units 110; a set of user interface and/or input-output devices (e.g., one or more computer or embedded system keyboards or keypads, and display devices); a set of communication units and/or network interfaces 120 configured for wireless and/or wire-based data communication; a bottom surface 3D inspection, imaging, or scanning station or apparatus 130 (e.g., which includes a 3D scan line profile generation apparatus or set of devices); a top surface 3D inspection, imaging, or scanning station or apparatus 140 (e.g., which includes a 3D scan line profile generation apparatus or set of devices); a sidewall inspection, imaging, or scanning apparatus 150; and a memory 200. An operating system 210, an imaging dataset memory, storage, and/or database 220, and various software modules or program instruction sets reside within the memory 200. In a representative embodiment, such program instruction sets include at least one program instruction set 230 configured for managing or controlling operations performed by a bottom surface 3D inspection station 130; at least one program instruction set 240 configured for managing or controlling operations performed by a top surface 3D inspection station 140; at least one program instruction set 250 configured for managing or controlling operations performed by a sidewall inspection station 150; at least one program instruction set 260 configured for generating 3D composite images; at least one program instruction set 270 configured for generating TPT and/or TMT values such as described herein; and possibly at least one program instruction set 280 configured for analysing, evaluating, or characterizing object characteristics or properties based on a generated 3D composite image and/or TPT and/or TMT values corresponding thereto.

In the above description, non-limiting representative example systems, subsystems, apparatuses, devices, and processes in accordance with particular embodiments of the present disclosure have been described. It will be readily understood by a person having ordinary skill in the relevant art that various modifications can be made to specific forms, arrangements, and/or structures of the embodiments described above, without departing from the scope of embodiments in accordance with the present disclosure, which is limited only by the following claims.

The invention claimed is:

1. A method for 3D inspection of objects, each object comprising a main body having a top surface, a bottom surface, and a plurality of sidewalls vertically extending between the top surface and the bottom surface of the object in a z-axis direction, the method comprising:
    capturing a 3D profile image of the object bottom surface and generating a corresponding bottom surface 3D profile image dataset while (a) the object top surface freely rests upon a first object seating surface and the object is not subjected to external compressive forces other than the force of gravity, or (b) the object top surface is held by a first suction tip by way of suction force and forcible compression of the top surface of the object against a first reference structure distinct from a first suction tip is avoided;
    capturing a 3D profile image of the object top surface and generating a corresponding top surface 3D profile image dataset while (c) the object bottom surface freely rests upon the first or a second object seating surface and the object is not subjected to external compressive forces other than the force of gravity, or (d) the object bottom surface is held by the first or a second suction tip by way of suction force and forcible compression of the bottom surface of the object against each of the first reference structure and a second reference structure distinct from the second suction tip is avoided;
    capturing a plurality of sidewall images of the object and generating a corresponding sidewall image dataset; and
    generating a 3D composite image dataset corresponding to a 3D digital reconstruction or estimation of the object based upon or using the bottom surface 3D profile image dataset, the top surface 3D profile image dataset, and the sidewall image dataset.

2. The method of claim 1, wherein the bottom surface 3D profile image dataset is generated by way of a bottom surface 3D scan line imaging procedure performed across the area of the bottom surface of the object, and the top surface 3D profile image dataset is generated by way of a top surface 3D scan line imaging procedure performed across the area of the top surface of the object.

3. The method of claim 1, wherein the first object seating surface is planar with respect to the surface area of at least one of the top surface and the bottom surface of the object, and/or the second object seating surface is planar with respect to the surface area of at least one of the top surface and the bottom surface of the object.

4. The method of claim 1, wherein (a) the object top surface freely rests upon the first object seating surface and the object is not subjected to external compression forces other than the force of gravity during the capture of the 3D profile image of the object bottom surface, and (c) the object bottom surface freely rests upon the first or a second object seating surface and the object is not subjected to external compressive forces other than the force of gravity during the capture of the 3D profile image of the object top surface.

5. The method of claim 1, wherein:
    while capturing the 3D bottom surface profile, (a) the object top surface freely rests upon the first object seating surface and the object is not subjected to external compression forces other than the force of gravity during the capture of the 3D profile image of the object bottom surface, and while capturing the 3D top surface profile, (d) the object bottom surface is held by the first or the second suction tip by way of suction force and forcible compression of the bottom surface of the object against each of the first reference structure and a second reference structure is avoided; or
    while capturing the 3D bottom surface profile, (b) the object top surface is held by the first suction tip by way of suction force and forcible compression of the top surface of the object against the first reference structure is avoided, and while capturing the 3D top surface profile(c) the object bottom surface freely rests upon one of first seating structure and the second seating structure.

6. The method of claim 1, wherein the object comprises a packaged semiconductor device, and wherein one of the 3D profile image of the object top surface and the 3D profile image of the object bottom surface is captured while the object sits in a carrier, platform, or medium having a standardized design with respect to the semiconductor industry and which is used for storing or transporting packaged semiconductor devices.

7. The method of claim 6, wherein the standard carrier, platform, or medium comprises one of an industry standard tray, an industry standard boat, or an industry standard tape structure configured for carrying packaged semiconductor devices of predetermined sizes.

8. The method of claim 1, wherein generating the 3D composite image dataset comprises generating each of a bottom surface of curvature image dataset and a top surface of curvature image dataset.

9. The method of claim 8, wherein generating the bottom surface of curvature image dataset comprises:
    numerically determining an array of (x, y) values that defines a reference bottom surface plane corresponding to the physical bottom surface of the object; and
    numerically determining z-axis deviations between the bottom surface 3D profile image dataset and the reference bottom surface plane for each (x, y) value within the array of (x, y) values within the reference bottom surface plane.

10. The method of claim 9, further comprising storing the z-axis deviations between the bottom surface 3D profile image dataset and the bottom surface reference plane for each (x, y) value as a bottom surface profile (BSP) dataset comprising an (x, y) array of bottom surface profile values corresponding to physical object top surface non-uniformity relative to the z-axis.

11. The method of claim 10, wherein generating the top surface of curvature image dataset comprises:

numerically determining an array of (x, y) values that defines a reference top surface plane corresponding to the physical top surface of the object; and numerically determining z-axis deviations between the top surface 3D profile image dataset and the reference bottom surface plane for each (x, y) value within the array of (x, y) values within the reference bottom surface plane.

12. The method of claim 11, further comprising storing the z-axis deviations between the top surface 3D profile image dataset and the top surface reference plane for each (x, y) value as a top surface profile (TSP) dataset comprising an (x, y) array of top surface profile values corresponding to physical object top surface non-uniformity relative to the z-axis.

13. The method of claim 12, wherein generating the 3D composite image dataset further comprises digitally aligning or registering the BSP dataset, the TSP dataset, and the sidewall image dataset relative to each other, and stitching together the digitally aligned or registered BSP dataset, TSP dataset, and sidewall dataset.

14. The method of claim 12, further comprising generating a True Object Main Body Thickness (TOMBT) dataset in which any given TOMBT(x, y) value represents a z-axis distance between the TSP and the BSP within the 3D composite image at a specific (x, y) point.

15. The method of claim 1, further comprising determining a Total Object Thickness (TOT) value by way of analysing the 3D profile image of the object bottom surface and the 3D profile image of the object top surface; and determining a largest z-axis distance between a lowest physical object structure in the 3D profile image of the object bottom surface and a highest physical object structure in the 3D profile image of the object top surface.

16. A system for 3D inspection of objects, each object comprising a main body having a top surface, a bottom surface, and a plurality of sidewalls vertically extending between the top surface and the bottom surface of the object in a z-axis direction, the apparatus comprising:

a set of 3D object imaging or scanning stations configured for imaging or scanning each of the object bottom surface and the object top surface and generating a 3D object bottom surface dataset and a 3D object top surface dataset, respectively, by way of:

(i) capturing a 3D profile image of the object bottom surface and generating a corresponding bottom surface 3D profile image dataset while (a) the object top surface freely rests upon a first object seating surface and the object is not subjected to external compressive forces other than the force of gravity, or (b) the object top surface is held by a first suction tip by way of suction force and forcible compression of the top surface of the object against a first reference structure distinct from a first suction tip is avoided; and (ii) capturing a 3D profile image of the object top surface and generating a corresponding top surface 3D profile image dataset while (c) the object bottom surface freely rests upon the first or a second object seating surface and the object is not subjected to external compressive forces other than the force of gravity, or (d) the object bottom surface is held by the first or a second suction tip by way of suction force and forcible compression of the bottom surface of the object against each of the first reference structure and a second reference structure distinct from the second suction tip is avoided;

an object sidewall scanning station configured for imaging or scanning a plurality of object sidewalls;

at least one processing unit; and a memory storing a set of program instructions configured for generating a 3D composite image dataset corresponding to a 3D digital reconstruction or estimation of the object based upon or using the bottom surface 3D profile image dataset, the top surface 3D profile image dataset, and the sidewall image dataset.

17. The system of claim 16, wherein the set of 3D object imaging or scanning stations comprises at least one 3D scan line profile imaging apparatus.

18. The system of claim 16, wherein the object sidewall scanning station comprises an apparatus configured for simultaneously imaging or scanning multiple object sidewalls.

* * * * *